(12) United States Patent
De La Huerga

(10) Patent No.: US 6,516,321 B1
(45) Date of Patent: Feb. 4, 2003

(54) METHOD FOR DATABASE ADDRESS SPECIFICATION

(76) Inventor: Carlos De La Huerga, 9190 N. Upper River Rd., Milwaukee, WI (US) 53217

( * ) Notice: Subject to any disclaimer, the term of this patent is extended or adjusted under 35 U.S.C. 154(b) by 0 days.

(21) Appl. No.: 09/374,568

(22) Filed: Aug. 13, 1999

Related U.S. Application Data

(63) Continuation-in-part of application No. 09/326,177, filed on Jun. 4, 1999, which is a continuation-in-part of application No. 09/247,349, filed on Feb. 10, 1999, which is a continuation-in-part of application No. 09/130,934, filed on Aug. 7, 1998, which is a continuation-in-part of application No. 09/112,062, filed on Jul. 17, 1998

(60) Provisional application No. 60/023,126, filed on Jul. 30, 1996.

(51) Int. Cl.⁷ .............................................. G06F 17/30
(52) U.S. Cl. .............................. 707/102; 707/1; 707/3; 707/513; 707/501
(58) Field of Search ................................ 707/513, 501, 707/102, 1, 3

(56) References Cited

U.S. PATENT DOCUMENTS

| | | | |
|---|---|---|---|
| 4,384,288 A | * 5/1983 | Walton | 340/825.34 |
| 4,864,501 A | 9/1989 | Kucera et al. | |
| 4,887,212 A | * 12/1989 | Zamora et al. | 364/419 |
| 4,994,966 A | 2/1991 | Hutchins | |
| 5,204,947 A | 4/1993 | Bernstein et al. | |
| 5,233,513 A | 8/1993 | Doyle | |
| 5,297,249 A | 3/1994 | Bernstein et al. | |
| 5,319,711 A | * 6/1994 | Servi | 380/23 |
| 5,404,435 A | 4/1995 | Rosenbaum | |
| 5,418,942 A | 5/1995 | Krawchuk et al. | |
| 5,434,974 A | * 7/1995 | Loucks et al. | 395/200 |
| 5,438,655 A | * 8/1995 | Richichi et al. | 395/142 |
| 5,515,534 A | * 5/1996 | Chuah et al. | 707/102 |
| 5,603,025 A | 2/1997 | Tabb et al. | |
| 5,608,900 A | 3/1997 | Dockter et al. | |
| 5,629,981 A | * 5/1997 | Nerlikar | 380/25 |
| 5,659,676 A | 8/1997 | Redpath | |
| 5,708,825 A | 1/1998 | Sotomayor | |
| 5,745,908 A | * 4/1998 | Anderson et al. | 707/513 |
| 5,764,906 A | * 6/1998 | Edelstein et al. | 395/200.49 |
| 5,781,900 A | 7/1998 | Shoji et al. | |
| 5,794,050 A | * 8/1998 | Dahlgren et al. | 395/708 |
| 5,806,079 A | 9/1998 | Rivette et al. | |
| 5,815,830 A | 9/1998 | Anthony | |
| 5,819,092 A | 10/1998 | Ferguson et al. | |
| 5,822,539 A | 10/1998 | van Hoff | |
| 5,822,720 A | 10/1998 | Bookman et al. | |
| 5,860,073 A | 1/1999 | Ferrel et al. | |
| 5,862,325 A | 1/1999 | Reed et al. | |
| 5,875,446 A | 2/1999 | Brown et al. | |
| 5,878,421 A | 3/1999 | Ferrel et al. | |
| 5,884,302 A | * 3/1999 | Ho | 707/3 |
| 5,895,461 A | * 4/1999 | De La Huerga et al. | 707/1 |
| 5,905,866 A | 5/1999 | Nakabayashi et al. | |
| 5,963,205 A | 10/1999 | Sotomayor | |
| 5,963,950 A | 10/1999 | Nielsen et al. | |
| 5,974,413 A | 10/1999 | Beauregard et al. | |
| 6,014,677 A | * 1/2000 | Hayashi et al. | 707/501 |
| 6,031,537 A | 2/2000 | Hugh | |
| 6,038,573 A | 3/2000 | Parks | |
| 6,094,649 A | 7/2000 | Bowen et al. | |
| 6,128,635 A | 10/2000 | Ikeno | |
| 6,151,624 A | 11/2000 | Teare et al. | |
| 6,178,434 B1 | 1/2001 | Saitoh | |
| 6,272,505 B1 | * 8/2001 | De La Huerga | 707/501 |

* cited by examiner

Primary Examiner—Frantz Coby
(74) Attorney, Agent, or Firm—Quarles & Brady, LLP

(57) ABSTRACT

A method for use with a processor which automatically creates hyperlinks between references to records in a record set which appear in a second record and the records in the record set, the method for eliminating ambiguity when record references overlap and including steps whereby resolution rules are applied which recognize references to a subset of records which are referenced by overlapping references and also a method for recognizing specific record information as a particular type and inserting tags which can be used by certain applications to identify the specific information within the record.

194 Claims, 21 Drawing Sheets

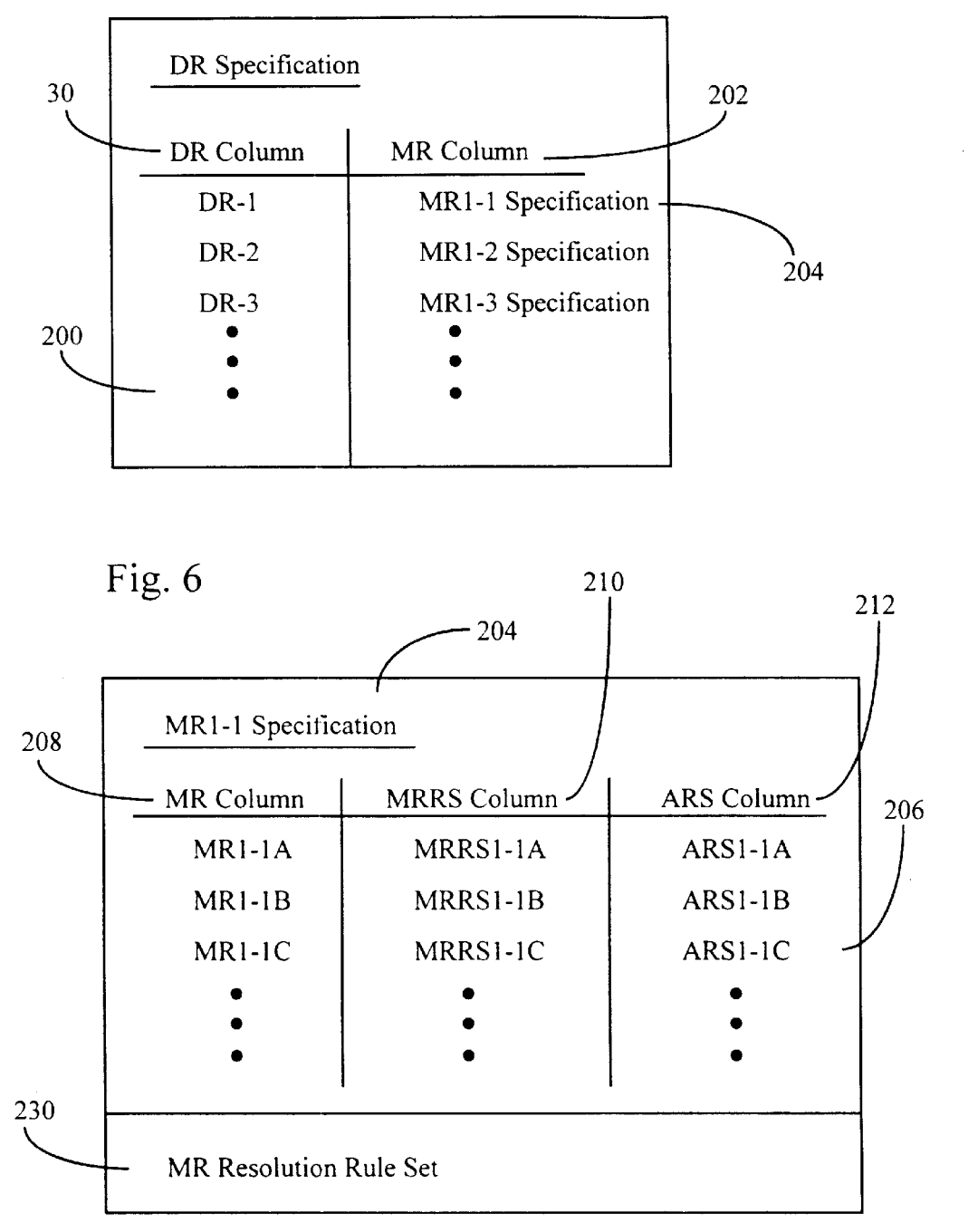

| DR Specification | |
|---|---|
| DR Column | MR Column |
| DR-1 | MR1-1 Specification |
| DR-2 | MR1-2 Specification |
| DR-3 | MR1-3 Specification |
| ⋮ | ⋮ |

Fig. 6

| MR1-1 Specification | | |
|---|---|---|
| MR Column | MRRS Column | ARS Column |
| MR1-1A | MRRS1-1A | ARS1-1A |
| MR1-1B | MRRS1-1B | ARS1-1B |
| MR1-1C | MRRS1-1C | ARS1-1C |
| ⋮ | ⋮ | ⋮ |
| MR Resolution Rule Set | | |

Fig. 7

MR1-1 Specification

| MR1-1 Column | MRRS1-1 Column | MR2 Spec. Column |
|---|---|---|
| MR1-1A | MRRS1-1A | MR2-1 Spec. |
| MR1-1B | MRRS1-1B | MR2-2 Spec |
| MR1-1C | MRRS1-1C | MR2-3 Spec. |
| ⋮ | ⋮ | ⋮ |

Fig. 9

MR2-1 Specification

| MR2-1 Column | MRRS2-1 Column | ARS2-1 Column |
|---|---|---|
| MR2-1A | MRRS2-1A | ARS2-1A |
| MR2-1B | MRRS2-1B | ARS2-1B |
| MR2-1C | MRRS2-1C | ARS2-1C |
| ⋮ | ⋮ | ⋮ |

Resolution Rule Set

DR/Address Look Up Table — 270

| DR (272) | Address (274) |
|---|---|
| "ECG Procedure" | Add-A — 278 |
| "X-ray Procedure" | Add-B |
| ⋮ | ⋮ |
| "Breast Cancer Bulletin" | Add-Q — 282 |
| "Colon Cancer Bulletin" | Add-R |
| ⋮ | ⋮ |

276 — "ECG Procedure"
280 — "Breast Cancer Bulletin"

Fig. 12

XML Specification — 290

| XML Type (298) | XMLRS (292) | XML Begin Tag (294) | XML End Tag (296) |
|---|---|---|---|
| Patient ID | XMLRS-1 | BT-1 | ET-1 |
| Heart Rate | XMLRS-2 | BT-2 | ET-2 |
| Image | XMLRS-3 | BT-3 | ET-3 |
| ⋮ | ⋮ | ⋮ | ⋮ |
| Abstract | XMLRS-Q | BT-Q | ET-Q |
| Diagnosis | XMLRS-Q+1 | BT-Q+1 | ET-Q+1 |
| Prescription | XMLRS-Q+2 | BT-Q+2 | ET-Q+2 |
| ⋮ | ⋮ | ⋮ | ⋮ |

300 — Patient ID
302 — Heart Rate
304 — Image
306 — Abstract
308 — Diagnosis
310 — Prescription
312 — XMLRS-1

| XML Specification | | | |
|---|---|---|---|
| XML Type | XMLRS | XML Begin Tag | XML End Tag |
| "Title" | XMLRS-1 | BT-1 | ET-1 |
| "Cross Reference" | XMLRS-2 | BT-2 | ET-2 |
| "Background" | • | • | • |
| "Summary" | • | • | • |
| "Brief Description of Drawings" | XMLRS-5 | BT-5 | ET-5 |
| - Fig. 1 | XMLRS-5-1 | BT-5-1 | ET-5-1 |
| - Fig. 2 | XMLRS-5-2 | BT-5-2 | ET-5-2 |
| - Fig. 3 | XMLRS-5-3 | BT-5-3 | ET-5-3 |
| • | • | • | • |
| "Claims" | XMLRS-7 | BT-7 | ET-7 |
| - Claim 1 | XMLRS-7-1 | BT-7-1 | ET-7-1 |
| - Claim 2 | XMLRS-7-2 | BT-7-2 | ET-7-2 |
| - Claim 3 | XMLRS-7-3 | BT-7-3 | ET-7-3 |
| • | • | • | • |

Fig. 16

XMLRS-5 (Corresponds to Description of Drawings)

Rule Set

- Search for segment:
    - After Summary end tag;
    - Before Detailed Description;
    - Natural Language search for:
        "Description of Drawings";
    - Must include at least one Figure of
        drawing description.

Fig. 17

XMLRS-7 (Corresponds to Claims)

Rule Set

- Search for segment:
    - Including "Claims" title;
    - After title, "1" must appear within 10
        terms followed by a single sentence
        ending in a period;
    - Search entire specification.

Fig. 18

XMLRS-5-1 (Corresponds to Figure 1 of Description of Drawings)

Rule Set

- Search for segment:
    - Which meets all XMLRS-5 requirements;
    - Which begins with "Fig. 1" and ends with a period or a semi-colon; and
    - Which is followed by a paragraph beginning with "Fig. 2" or a permutation thereof.

Fig. 19

XMLRS-5-1 (Corresponds to Claim 1 of the Claims)

Rule Set

- Search for a segment:
    - Which meets all XMLRS-7 requirements;
    - Begins with a "1" followed by a single sentence and ends with a period; and
    - Which is followed by a paragraph beginning with a "2".

Fig. 20

METHOD FOR DATABASE ADDRESS SPECIFICATION

CROSS-REFERENCE TO RELATED APPLICATIONS

This application is a continuation-in-part of a U.S. patent application Ser. No. 09/326,177 which is titled "Method for Specifying Enterprise-wide Database Address Formats" which was filed on Jun. 4, 1999 by the present inventor which was a continuation-in-part of U.S. pat. appln. Ser. No. 09/247,349 which was filed on Feb. 10, 1999 and is entitled "Method and System for Automated Data Storage and Retrieval" which claimed priority from U.S. pat. appln. Ser. No. 08/727,293 which was filed on Oct. 9, 1996 and is entitled "Method and System for Automated Data Storage and Retrieval With Uniform Address Scheme" which in turn claims priority from provisional Appln. Ser. No. 60/023,126 which was filed on Jul. 30, 1996, the 09/247,349 application also claiming priority from U.S. pat. appln. Ser. No. 08/871,818 which was filed on Jun. 9, 1997 and is entitled "System and Method for Translating, Collecting and Archiving Patient Records". This application is also a continuation-in-part of U.S. pat. appln. Ser. No. 09/130,934 which was filed on Aug. 7, 1998 and is entitled "Method and System for Resolving Temporal Descriptions of Data Records in a Computer System". This application is also a continuation-in-part of U.S. pat. appln. Ser. No. 09/112,062 which was filed on Jul. 17, 1998 and is entitled "Word Processor With Hyperlink limitation".

STATEMENT REGARDING FEDERALLY SPONSORED RESEARCH OR DEVELOPMENT

Not applicable.

BACKGROUND OF THE INVENTION

The present invention relates to information processors and more particularly to a search system for generating links to a first information set which is referenced in a second information set and to a system which automatically inserts tags into records which can be used by other applications to identify specific types of information within the record.

The computer networking industry is constantly searching for new and improved ways to facilitate communication between network users and to access and manipulate data stored on network databases. To this end one common way to access data stored on a network has been to employ universal resource locators (URLs) common to the Internet. A URL is essentially an address which includes a plurality of fields which together operate as a pointer to information stored at a specific database address on a network. The address fields typically include two general information types including server specifier and specific data information. The server specifier information specifies a server which is linked to a database which includes specific information required. The specific data information provides a key which can be used by a server to determine the precise data required by a URL. For example, a first and typically broadest field for data stored on a hospital database may identify the hospital server (e.g., St. Mary's, Springfield, historical server). A narrower field may include specific data information indicating a specific hospital patient (e.g., a nine digit patient ID number).

When a URL is transmitted, the network routes the URL to the URL specified server. When the server receives the URL, the server parses the URL to identify the specific data information, retrieves the information and then performs some function (e.g., manipulation, providing the information back to the requesting network user, etc.) on the retrieved information.

One problem with URLs is that servers rely heavily on URL fields to identify URL specified data. As networks become more complex and as users and applications require access to relatively more specific data, additional fields are added to URLs and the URL scheme becomes much more complicated. For example, initially a hospital may include only a single server and therefore, once the hospital is specified in a single URL field, the server is known. However, as the hospital system expands and additional servers are added to the hospital system, additional server specifying fields need to be added. As another example, in a primitive system it may be sufficient to access complete ECG records for physician review. However, as a system becomes more complicated it may become desirable to enable access to more specific ECG record data such as heart rate.

Accessing specific data is further complicated when an application requires many small data segments from one or more records. For example, in a physician's report it may be advantageous to link references within the report to specific data stored at addresses linked to the report via the network. For instance, the desired links may be to an image, a heart rate and a diagnosis for a particular patient. In this case, three separate URLs would have to be specified by a user and linked to referencing text in the report, one URL for each of the image, heart rate and diagnosis. While such linking is advantageous, in many cases such linking is never contemplated because of the complexity of the required URL addressing scheme.

Recently another method and tool for accessing/manipulating data within a specific record has been developed which specifies universal "tags" which can be used within a record to earmark specific data types. An exemplary "tagging" language is the extensible markup language (XML). The tags are to be used by processor applications which are familiar with the tags to identify specific information types. Applications which are capable of recognizing tags are referred to hereinafter as "tag enabled" and records which include such tags are likewise referred to as tag enabled. Tags are typically paired including a "begin" tag and an "end" tag identifying the beginning and the end of a specific data type within a corresponding record. For example, in a patient record, a "<patient id>" tag may specify the beginning of a field including a patient ID and a corresponding "</patient id>" tag may specify the end of the patient ID field. Similarly, a "begin image" tag may specify the beginning of an image field while an "end image" tag specifies the end of the image field. Using a URL scheme a record can be retrieved by a tag enabled application. Thereafter, the application parses the record to identify specific data types required by the application and uses the identified data types.

Thus, tags and tag enabled applications can be combined with URLs to overcome some of the complexity associated with URL data specification within a specific record. Nevertheless, linking record segments and references together via URLs and tags requires knowledge about URL and operation and formats. For example, to link a reference in a first record to a segment in a second record, first the second record address has to be specified and the segment tags have to be specified. Then, the URL address of the second record and the tags of the record segment to be linked have to be linked to the reference in the first record. Because many record producers (e.g., physicians) do not have required URL and tag knowledge, despite the advantages associated with such linking, most such linking is foregone.

U.S. patent application Ser. No. 09/326,177 (hereinafter "the '177 reference") entitled "Method for Specifying Enterprise-Wide Database Address Format" which was filed by the present inventor on Jun. 4, 1999 describes a system whereby URLs are automatically generated for data within a record thereby streamlining the process of linking references in one record to data stored at other network locations. To this end information in a first record is searched for data references (DRs) which reference other records. When a DR is identified, other record information is sought for constructing a URL address to the record associated with the data reference. After a URL corresponding to the record associated with the data reference is constructed, a link to the referenced record is formed. Exemplary links include hyperlinks, importation of the referenced record information into the referencing first record or electronic document, etc. Both real time and batch processing are contemplated.

A wrinkle of complexity is added to the referencing scheme whereby modifier references (MRs) may be used to further specify a specific record or record segment when a DR is identified. In this case, when a DR is identified, the record is further examined to identify modifier references (MRs) which identify a specific segment of a record which is associated with the data reference. When an MR is located, additional information is sought within the record for building an address to the record or record segment referenced by the DR/MR combination. Once again, a link is created between the referencing record and the referenced record or record segment.

Unfortunately, the '177 reference system also has several shortcomings in the area of html linking. The '177 reference recognizes that various search rules can be employed by a processor assigned the task of constructing referenced record addresses. Nevertheless, in the interest of simplifying explanation of the novel concepts in the '177 reference, the '177 reference assumes a simple searching rule wherein only the term immediately preceding a DR is examined to locate an MR. For example, where an ECG DR is located, only the term preceding the ECG term is sought for MRs (e.g., admission, post-op, etc.).

While such a simple MR search rule is advantageous for explanation purposes, it has been recognized that such a simple rule is most likely inadequate for most practical automatic linking systems for a number of reasons. First, such a simple rule would likely fail to identify many intended links. For instance, while many physicians may enter the phrase "post-op ECG" into a report, other physicians may enter the phrase "post-op exemplary ECG" to refer to a similar record. In this case, the intermediate term "exemplary" would render the phrase "post-op exemplary ECG" unrecognizable as a DR/MR combination. In fact, in this regard, an MR and a corresponding DR may be separated by several (e.g., 10) terms or an MR may follow a DR.

Second, even where a rule is adopted which accommodates terms between an MR and a DR, there may be instances where two DRs fit the required relationship with respect to a single MR or where two MRs fit the required relationship with respect to a single DR. For example, the phrase "post-op ECG and admission report" may be included in a record. In this case, a rule which specifies that an MR may be within five terms of a DR would be confusing as the exemplary phrase could reference a post-op ECG or an admission ECG or both.

Third, it has been recognized that in the case of certain advantageous linking features, simple address constructing rules may cause additional confusion. For example, it would be advantageous to have a system which supports more than a single MR level. For instance, where "ECG" is an exemplary DR, a first level MR (i.e., MR1) may be "post-op", indicating a post-operation ECG and a second level MR (e.g., MR2) may be "heartbeat waveform". While entering a report, a physician may reference a "post-op ECG heartbeat waveform" corresponding to a specific segment of a post-op ECG report which includes a heartbeat waveform. In this case, the system may support links to an entire ECG report (for example, the most recent ECG report), an entire post-op ECG report (independent of whether or not the post-op ECG report is the most recent report), a graph corresponding to the post-op ECG heartbeat waveform, a graph corresponding to a most recent ECG heartbeat waveform, or to any combination of an ECG report, a post-op ECG report, the post-op ECG heartbeat waveform or the most recent ECG heartbeat waveform. Unfortunately, there is no way for a processor to determine which of several links should be formed using a simple rule such as checking the term prior to a DR to identify an MR.

Therefore, it would be advantageous to have a method and apparatus which facilitates unambiguous linking between record references in a first record and referenced records or segments in a second record. In addition, it would be advantageous to have a method and apparatus for automatically inserting markup language tags such as XML on HTML into records either as the records are formed or in a batch mode.

BRIEF SUMMARY OF THE INVENTION

Hereinafter the term "specifying reference" (SR) will be used to refer generically to each of a DR and a DR/MR combination or a DR/MR/MR combination.

An exemplary embodiment of the invention includes a system wherein link ambiguity is rendered unambiguous by imposing a rule set which specifies which of two or more SRs should be selected when two or more SRs and overlap. It has been recognized that in most cases when two possible DR/MR combinations or DRs, which overlap are identified, the user wishes to form a link to a record segment associated with the longer of the two SRs as the longer of the SRs typically more specific than the shorter. Therefore, a preferred rule is that the longest of two SRs is selected. For example, when a first DR/MR combination is "previous ECG" and a second DR/MR combination is "previous ECG report", a link is formed to the combination "previous ECG report" as that reference is the longest and most specific.

The invention also includes a system wherein link ambiguity between DRs or MRs which are associated with more than one other DR or MR is rendered unambiguous through specification of rules used to select one DR/MR combination over another. For example, where the term "previous" is proximate both DRs "ECG" and "X-ray" such that the term previous could modify either of the two DRs, a rule set is specified which enables the system to select one DR/MR combination over the other. For instance, the rule set may specify that when a single MR is proximate two DRs, the system selects the DR/MR combination corresponding to the first DR or corresponding to the DR which is closest to the MR. Other rule sets, are contemplated, the important characteristic of the sets being that some rule set is provided to minimize ambiguity.

In addition, the invention also includes a system wherein, instead of building URLs when an SR is identified, a processor uses a lookup table to identify a suitable URL which corresponds to the identified SR. For example, in the case of a medical facility, medication information and dosing regimen may routinely be referenced in patient records. In this case, where each brochure and schedule is electronically stored at a known address and can be referenced by a specific SR, the SRs and known addresses are correlated and stored in a lookup table. When an SR is recognized in a record, the table is accessed, the address corresponding to the SR is identified and a link is formed. This aspect of the present invention is particularly useful where a small number of records may routinely be referenced in other records.

Moreover, the invention also includes a system which automatically inserts tags into records to render the records useful in tag enabled applications. To this end, it has been recognized that record segments which are often related to specific types of data will have a specific and recognizable format or will include specific text or graphical indicia. Because the formats, text and/or indicia are recognizable, the information in the formats can be identified as a specific type by a processor which is programmed to search for and identify such information. Once a segment type is known, tags which can be recognized by a tag enabled application can be inserted in the record which is then tag enabled (i.e. can be used by the tag enabled application).

Thus, one object of the present invention is to eliminate ambiguity between SRs where two SRs overlap or a shorter SR is included within a longer SR.

Another object of the invention is to automatically determine whether or not tags (e.g. may suitably be added to a record to identify specific record segments and information types therein and, when appropriate, to automatically add the tags to render the record tag enabled so that a tag enabled application can identify specific information within the record.

One other object of the invention is to ensure that, when modifications are made to a record which includes tags, the tags remain correct. To this end, the invention includes a feature whereby a processor monitors modifications to a record which includes tags and, when a modification effects tag correctness, the processor performs one of several different functions to ensure that incorrect tags are removed from the record. To this end, one function may be to eliminate all tags in the record. An extended function may be to, after eliminating all tags, reinsert tags into the record where appropriate. Other functions are contemplated.

One other object of the invention is to facilitate a simpler linking process for linking references to a first record which appear in a second record to the first record. To this end, a look-up table is used.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

BRIEF DESCRIPTION OF THE SEVERAL VIEWS OF THE DRAWINGS

FIG. 6 is a schematic diagram illustrating another DR specification;

FIG. 7 is an expanded schematic diagram of one of the MR specifications of FIG. 6;

FIG. 9 is a schematic diagram illustrating another MR specification according to the present invention;

FIG. 10 is a schematic diagram of our exemplary second level MR specification according to the present invention;

FIG. 11 is a schematic diagram of an exemplary DR look-up table according to the present invention;

FIG. 12 is schematic diagram of an exemplary XML specification according to the present invention;

FIG. 16 is a schematic diagram of another XML specification according to the present invention;

FIG. 17 is detailed schematic diagram illustrating an exemplary XMLRS of FIG. 16;

FIG. 18 is similar to FIG. 17, albeit illustrating another XMLRS of FIG. 16;

FIG. 19 is a schematic illustrating a nested XMLRS of FIG. 16;

FIG. 20 is similar to FIG. 19, albeit illustrating a second nested XMLRS of FIG. 16;

FIG. 27a is a schematic diagram illustrating a description box according to the present invention while

DETAILED DESCRIPTION OF THE INVENTION

Although the present invention is meant to be used in a plurality of different environments, in order to simplify this explanation, unless indicated otherwise, the invention will be described in the context of a medical facility named "St. Mary's, Springfield". In addition, while the present invention is described in the context of a wordprocessor, the present invention is meant to be used in conjunction with other data manipulation programs such as database management programs, spread sheet programs, etc. Moreover, while some of the examples hereinafter are presented in the context of real time processing and others are presented in the context of batch processing, each real time example could be performed in batch and vice versa.

Furthermore, while other "tagging" languages are contemplated and may be used with the present invention, the invention will be described herein in the context of XML and XML tags. Nevertheless, it should be understood that the invention is not to be so limited.

Throughout this specification the phrase "natural language processing" is used to describe one type of search capability in various contexts. Natural language processing is well known in the word processing art and has been described in some detail in a several previously issued U.S. patents including U.S. Pat. Nos. 4,887,212, 4,994,966, 5,884,302 and 5,794,050, each of which are incorporated herein by reference for the purpose of generally teaching the concepts which together comprise natural language processing. Generally, natural language processing constitutes a system whereby a processor can use rules which are generally acceptable within a language to determine the meaning of a string of words. For example, the processor is typically equipped to recognize words and phrases as prepositional phrases, nouns, verbs, adjectives and also can identify relationships between proximate words and phrases. For instance, if the exemplary phrase "ECG report and x-ray image" were considered, the processor could recognize that the term "ECG" modifies the term "report" while the term "x-ray" modifies the term "image." The patents referenced above should be relied on for additional teachings in this regard.

Figure 1:
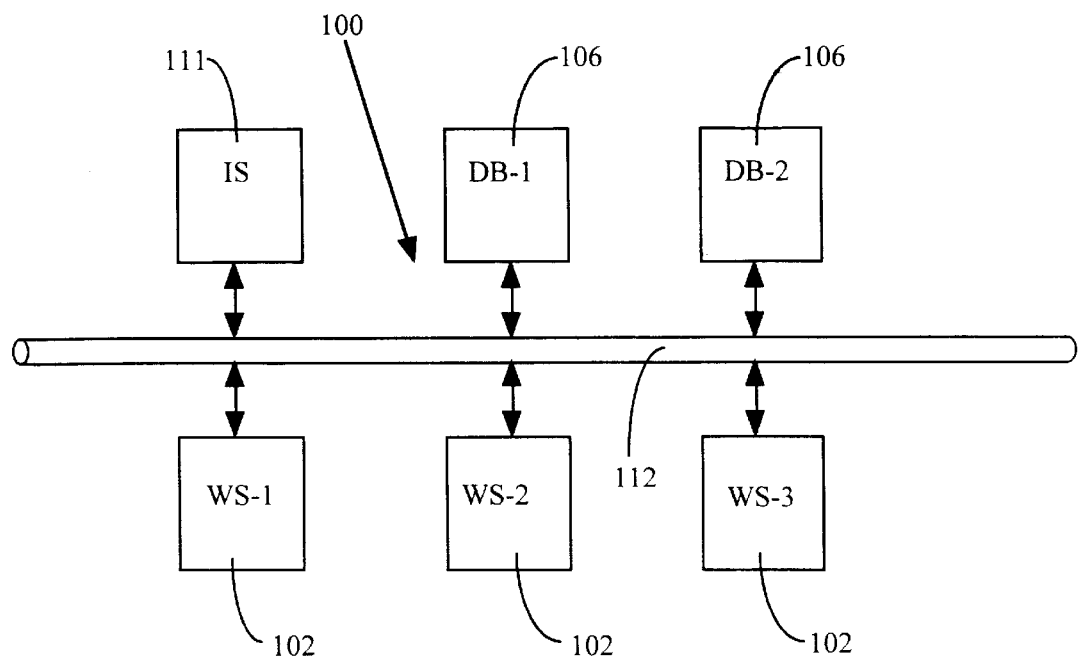
FIG. 1 is a schematic diagram of a computer network used with the present invention.

Referring now to the drawings wherein like reference characters and numbers represent like components, data constructs and signals throughout the several views and, specifically, referring to FIG. 1, the invention is illustrated as a computer network 100 including a plurality of workstations 102 which may be personal computers, hand held devices, etc., and a plurality of databases 106. Network 100 also includes an Information System (IS) 111. Databases 106, system 111 and workstations 102 may communicate with each other via a communication network 112 which may be a combination of local and wide area networks using Ethernet, serial line, wireless, or other communication standards. Network 112 may also be arranged so as to be part of the Internet or as an individual Intranet.

Figure 2:
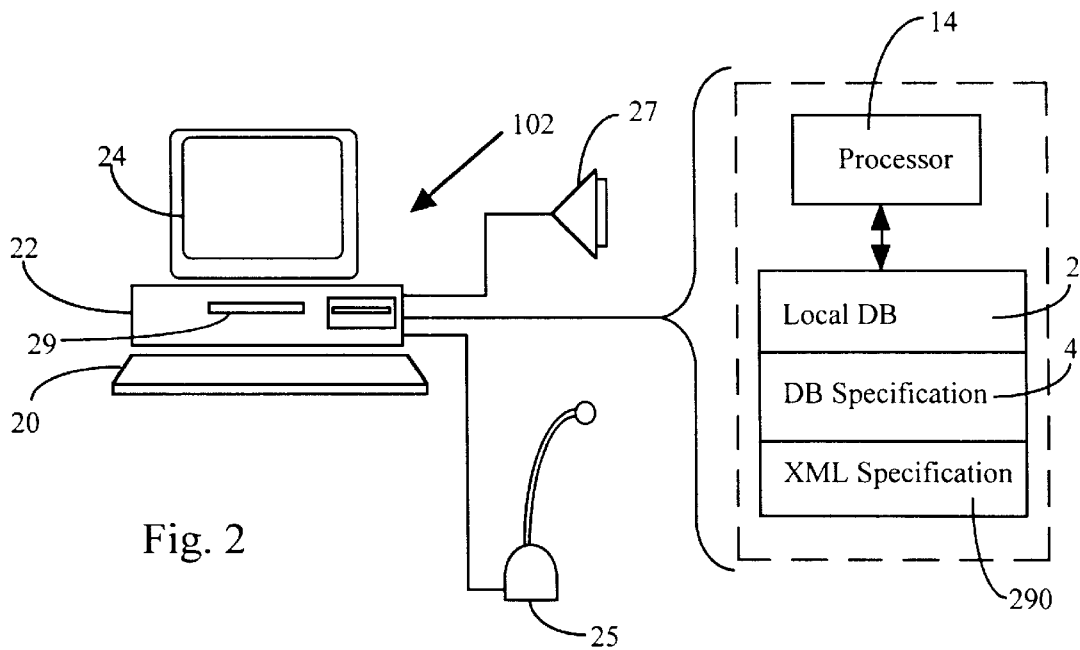
FIG. 2 is a schematic diagram of a work station of FIG. 1.

Referring to FIG. 2, each workstation 102 includes user interface hardware including a keyboard 20, a computer 22 and a video display 24. In addition, as illustrated, the hardware may also include other data input devices such as a microphone 25 supported by voice recognition software (not illustrated), a wireless data link 27 for receiving data from a remote information collection device (not illustrated), a disk drive 29 linked to computer 22 to receive data via a disc or the like, or any other data receiving devices. Computer 22 includes a processor 14 which is linked to a local DB2 and supports a network browser or similar display, entry and retrieval program.

Wordprocessor 14 runs under the direction of computer 22 and performs all of the functions (e.g., creation of documents, modification of documents, storage and retrieval, etc.) which are typically associated with a conventional word processor. In addition, processor 14 is also capable of additional functions including recognition of data references (DRs) in data records, identification of hypertext links between the DRs and data records, recognition of XML information segments within records and insertion of XML tags to render records tag enabled. Various characteristics of wordprocessor 14 which facilitate these features are described separately below.

1. Creating Unambiguous Record Links

A U.S. patent application Ser. No. 09/326,177 now pending entitled "Method for Specifying Enterprise-Wide Database Formats" (hereinafter "the '177 reference") which was filed on Jun. 4, 1999 by the present inventor teaches, among other things, a system wherein a wordprocessor can form links between references to a record and the referenced record when the references appear in a second record. The '177 reference specification is incorporated herein by reference. Nevertheless, some characteristics of the system described in the '177 reference which are particularly pertinent to the present invention are repeated here in the interest of clarity.

Referring still to FIG. 2, local DB 2 includes DR specification 4 which is accessible and useable by processor 14 to create links between references to a first record and the first record when the references appear in a second record. To this end, referring also to FIG. 3, specification 4 includes both a DR table 5 and a DR resolution rule set (RRS) 7. Table 5 includes two columns including a DR column 30 and an address rule set (ARS) column 32.

DR column 30 includes a list of DRs. A DR is a unique phrase or word which may be used in a record to refer to another record or record segment. In the context of a medical facility an exemplary DR may be as simple as "medication given", "ECG report", or "Admission NMR heartbeat". As explained in more detail below, when a processor linking feature is selected, processor 14 searches for DRs in a specified record and, when a DR is identified, links the DR to a record or record segment associated with the DR via a hyperlink or other mechanism. In the preferred embodiment of the invention the longest DRs in a DR list include more than one word.

ARS column 32 includes a separate ARS for each DR in column 30. Exemplary ARS-1 is identified by numeral 44. In one embodiment which includes relatively complex ARSs each ARS includes a plurality of related data constructs which together define an address format for the corresponding DR in column 30, define rules for identifying information for forming an address having the address format and define rules for using the identified information to form an address. To this end, referring to FIG. 4, exemplary ARS 44 specifies an address format including six address fields 56, 58, 60, 62, 64 and 66.

For each field, ARS 44 specifies that the field is either "fixed" or "variable". Fixed means that the text (i.e. data object) used to instantiate a field is always the same. For example, for St. Mary's of Springfield, it will be assumed that all DBs are identified generally by a universal resource locator (URL) segment "http://hww.st_mary.springfield". In this case, all DRs include a first fixed field 56 wherein the text to instantiate the field comprises: http://hww.st_mary.springfield". As another example, each time a medication is given to a patient, an administration record is required. In this case, an exemplary fixed text field specifying the occurrence of medication administration is "medication/given".

Figure 4:
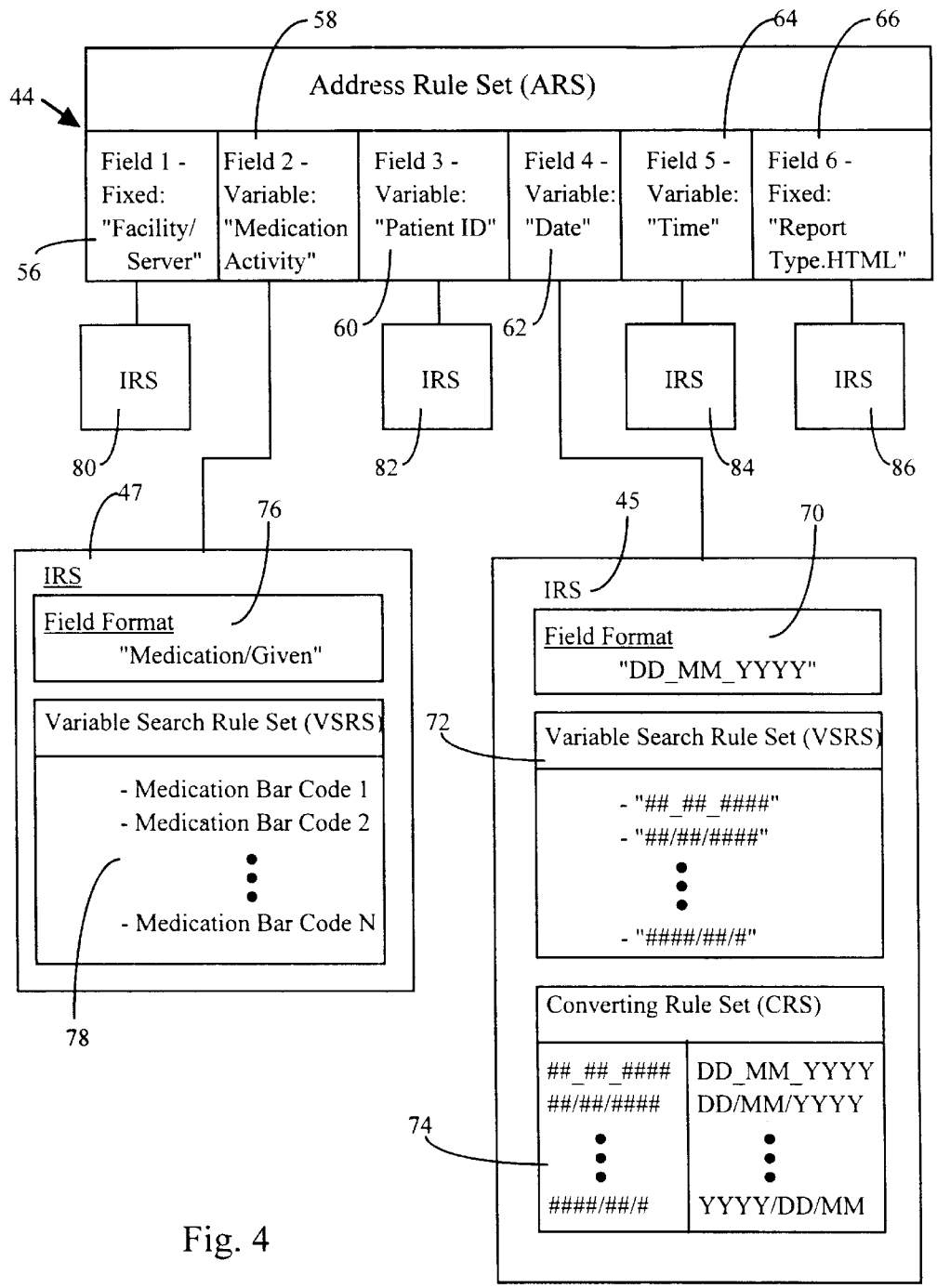
FIG. 4 is a schematic diagram of an exemplary ARS of FIG. 3.

Referring still to FIG. 4, variable means that text used to fill or instantiate a field may vary from record address to record address. For example, the character string used to fill a date field will vary daily, the character string used to fill a time field will vary as time lapses and the character string used to fill a patient field will vary depending on which patient a record is associated with. In FIG. 4, fields 56, 58 and 66 are fixed while fields 60, 62 and 64 are variable.

In addition to specifying fixed and variable characteristics, ARS 44 also specifies a field name for each field. For example, for fixed fields 56, 58 and 66 ARS 44 specifies "facility/server", "medication/given" and "report.html". For variable field 60, ARS 44 specifies name "patient ID", for field 62 ARS 44 specifies name "Date" and for field 64 ARS 44 specifies name "Time". These field names are not required by processor 14 but rather are provided to help a system user define data type definitions and to visualize address and record formats. To this end, the field names should generally describe the type of information corresponding to the field. Hence the name "Date" corresponds to the date field and so on.

For each field 56–66, ARS 44 also provides a field instantiation rule set (IRS). As the characteristics of each IRS are similar, only IRSs 45 and 47 corresponding to fields 62 and 58, respectively, are illustrated and described in detail. IRS 45 includes a field format 70, a variable search rule set (VSRs) 72 and a conversion rule set (CRS) 74. Similarly, IRS 47 includes a field format 76 and a variable search rule set (VSRs) 78.

For fixed field 58, field format 76 constitutes the specific fixed text to be placed in the field. For example, for field 58, the field format includes "medication/given". VSRs 78 includes a rule set which provides rules which indicate how, based on a set of information, to determine that medication has been given. For example, rules to determine if a medication has been given in the present example include a list of every possible medication bar code used at the St. Mary's facility. When one of the listed bar codes is identified in a set of information, medication administration is assumed. Although not illustrated, VSRs 78 may include other rules for determining if a medication has been administered. Although the rule sets described herein are relatively simple, other more complex rules are contemplated.

Referring still to FIG. 4, field format 70 constitutes a variable character string specifying an information format required to instantiate field 62 with a date. In the present example, the variable character string is "DD_MM_YYYY" where DD indicates the day of a month, MM indicates a number corresponding to the month of a year (i.e. "05" is May) and YYYY indicates a four digit year (e.g. 1996). Thus, independent of how a date appears in an information set, the date must be provided in the specified variable character string form "DD_MM_YYYY" according to format 70.

VSRs 72 includes a rule set which is used to search an information set for any date specifying information which can be used to instantiate variable field 62. To this end, VSRs 72 specifies a separate rule corresponding to each possible format in which a date might appear in an information set (see exemplary rules in VSRs 72). Exemplary rules include "##/##/####", "##_##_##" and "####_##_##" where each "#" corresponds to a number in the character string. Many other rules are contemplated including rules which account for spelled out months, other date patterns and so on.

Referring still to FIG. 4, with respect to variable field 62, while corresponding date specifying information may appear in a record or information set in any of several different formats, as indicated by format field 70, ARS 44 requires a specific format for instantiating variable field 62. Thus, conversion rules for converting date information to specific format 70 are required. To this end, CRS 74 includes conversion rules corresponding to field 62. In FIG. 4, an exemplary rule correlates "##/##/####" with "DD/MM/YYYY" meaning the first two "#'s" are assumed to correspond to "DD", the third and fourth "#'s" are assumed to correspond to "MM" and the last four "#'s" are assumed to correspond to "YYYY". Thus, if a string having the form "##/##/####" is located, format "DD/MM/YYYY" is assigned to corresponding numbers. Then, D's, M's and Y's in format "DD/MM/YYYY" can be mapped to D's, M's and Y's in field format 70 (i.e. into "DD_MM_YYYY") to make a data conversion and provide information to instantiate field 62 with a date having format 70. Similar IRSs (e.g. 80, 82, 84, 86) are provided for each of fields 56 through 66.

Referring again to FIGS. 2 and 3, assuming a complete DR specification 4 is stored on DB 2, a first record which includes at least some of the DRs in table 5 is currently accessed by processor 14 and that the record linking function of processor 14 has been selected. In this case, processor 14 searches the first record for DRs which appear in column 30. When a DR is identified, processor 14 accesses table 5 and identifies the ARS which corresponds to the identified DR. Thereafter, processor 14 uses the ARS to identify information required to construct an address for the record or record segment associated with the identified DR and the format of the information, gleans the required information from the first record (or from some other source, e.g., may request some information or retrieve information from other network 100 components), constructs an address identifying the referenced record and links the address to the identified DR.

Linking may include modifying the appearance of the identified DR and linking such that when the DR is selected (e.g., via a mouse controlled cursor), processor 14 uses the address to retrieve the referenced record and display the record for observation. Other linking characteristics are contemplated.

It has been recognized that some systems may support both long and short DRs wherein a long DR constitutes a short DR and some additional text. For example, one short DR may include the term "ECG" while a relatively longer DR includes the phrase "previous ECG". In this case, a system which operates as described above would likely result in some confusion. For instance, in this case the system would likely provide two separate links to the term "ECG", one link to an "ECG" document and another link to a "previous ECG" document.

According to the present invention, instead of allowing such ambiguity, an inventive rule set is imposed on the system whereby, when two or more DRs are identified within a record and one or more of the identified DRs is encompassed in a longer DR, the longer of the DRs is selected for forming an address and creating a link. Thus, in the present example where DRs "ECG" and "previous ECG" are both identified, processor 14 selects "previous ECG" for addressing and linking purposes.

Figure 3:
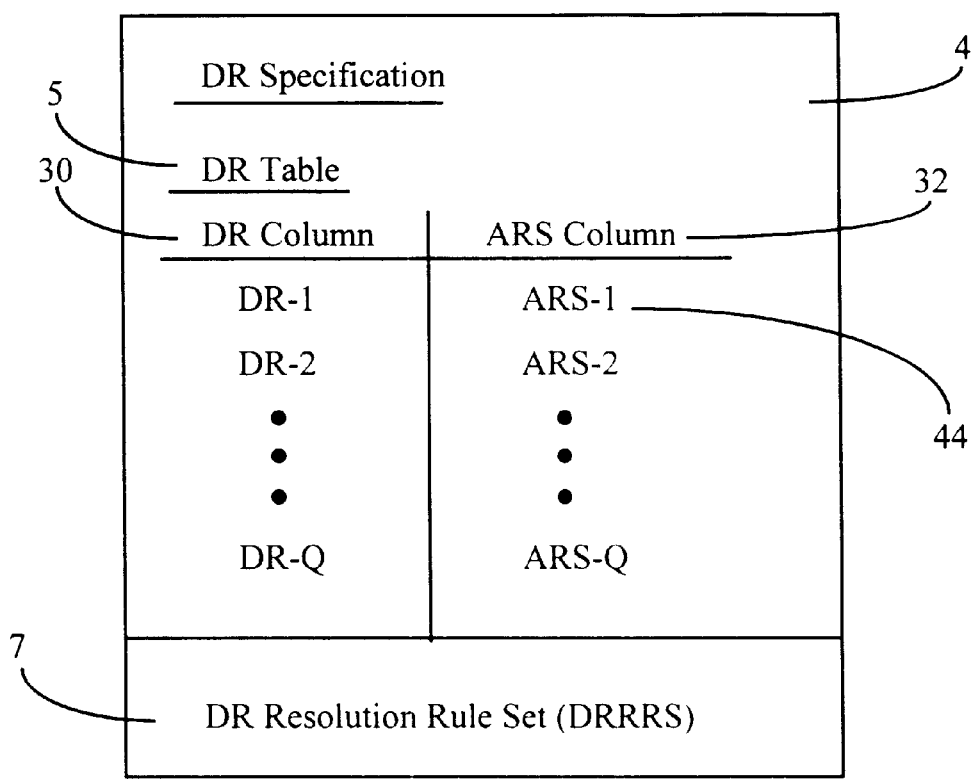
FIG. 3 is a schematic diagram of a DR specification according to the present invention.

To this end, referring still to FIGS. 2 and 3, DR RRS 7 specifies rules which facilitate selection of the longest of two DRs when one DR consists of another DR and additional text. Although the present invention includes preferred rules for carrying out the function of identifying the longest DR, in the broadest context of the invention, the manner in which RRS 7 performs this function is irrelevant. Nevertheless, this function should be performed efficiently. For example, in one system the longest possible DR may constitute a phrase including five terms. In this case, when a DR is recognized, prior to forming an address for the record corresponding thereto, processor 14 should check the five terms thereafter to ensure that the identified DR is not part of a longer DR. Where the identified DR is not a part of the longer DR the processor can form the address. However, where the identified DR is part of a longer DR, the processor should proceed to form an address corresponding to the longer of the two DRs.

According to one efficient search technique, DRs may be stored in an alphabetical table wherein, as terms and phrases are recognized as being parts of DRs, processor 14 begins with the longest possible DR corresponding to a phrase or text and moves on to shorter phrases or text only as additional terms or letters are considered. For instance, where three DRs are "ECG report heart rate", "ECG report" and "ECG", during data entry and real time processing, when the term "ECG" is entered, processor 14 initially assumes the longest DR "ECG report heart rate". Thereafter, assuming data entry next provides the term "report", processor continues to assume longest DR "ECG report heart rate". However, if the next term entered is "taken", processor 14 recognizes that longest DR "ECG report heart rate" is no longer valid and must search the alphabetical DR listing for the next longest and still valid DR. In this case the next longest valid DR is "ECG report". Thus, processor 14 selects the "ECG report" DR and forms an appropriate address for linking purposes. The above example is only exemplary and, for example, the process may be reversed whereby the shortest DRs are sought and as additional text is entered, processor 14 determines if longer DRs are entered. If additional text does not correspond to a longer DR, the shorter DR is identified and a corresponding address formed.

Another problem which can occur when attempting to form links between references in one record and records associated with the references is that DRs may overlap. For example, assume that two supported DRs consist of the phrases "admission ECG" and "ECG report" (i.e., here it is assumed the phrase "admission ECG report" is not supported). In this case, if the phrase "admission ECG report" appears in a record, which of the two supported DRs should be selected for addressing purposes is unclear and selecting both would be confusing.

To deal with this problem RRS 7 imposes another rule on processor 14 operation which requires processor 14 to select the first of several DRs when DRs overlap. Thus, in the present example, processor 14 would select DR "admission ECG" and would discard DR "ECG report".

Figure 5:
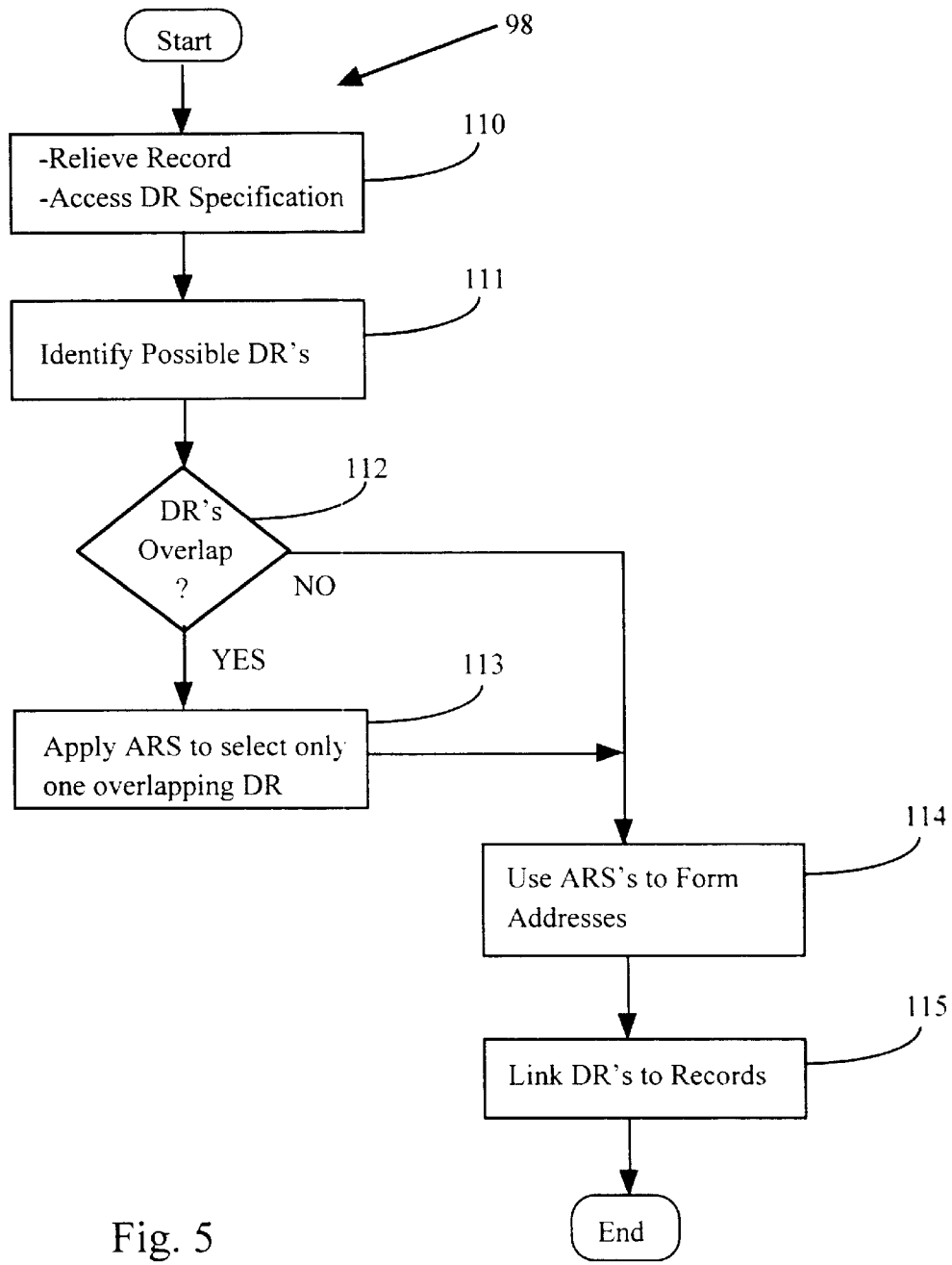
FIG. 5 is a flowchart illustrating an inventive method.

An exemplary DR selection process 98 which resolves ambiguity where DRs overlap is illustrated in FIG. 5. Referring also to FIGS. 2 and 3, at block 110 processor 14 receives a record and accesses DR specification 4. At block 111 processor 14 determines if any DRs overlap. Where no DRs overlap control passes to block 114 where processor 14 uses an ARS from table 5 to form addresses for each DR and at block 115 processor 14 links DRs to associated records via the created addresses. Where DRs overlaps at block 112 control passes to block 113 where processor 14 applies RRS 7 to select only one DR from each set of overlapping DRs. Then control passes to block 114 where addresses are only generated for unambiguous DRs which do not overlap.

The '177 application also contemplates a more complex system which supports additional levels of referencing for linking purposes. To this end, the '177 application recognizes that a single DR may be modified by any of several different modifier references (MRs) such that each DR/MR combination refers to a specific and distinct record or record segment and is correlated with a specific record or segment address. For example, a DR may comprise the term "ECG" while one MR may be "previous" and another MR may be "admission" so that DR/MR combinations include each of "admission ECG" and "previous ECG.".

Referring to FIG. 6, to support DR/MR combinations a slightly different DR specification 200 is required. Specification 200, like table 5, includes a DR column 30 which lists all possible DRs. However, instead of including an ARS column 32, specification 200 includes an MR specification column 202 which lists a separate MR specification for each DR in column 30. Exemplary MR specifications in column 202 are MR1-1, (i.e. 204) and MR1-2 which correspond to DR-1 and DR-2, respectively. The first number in each MR specification reference (i.e., "1" in MR1-1) indicates a first level (levels are described in more detail below) MR and the second number (i.e., "2" in MR1-2) indicates which DR the MR reference corresponds to. For example, MR1-1 is a first level MR and corresponds to DR-1 while MR1-2 is a first level MR and corresponds to DR-2.

Referring also to FIG. 7, specification 204 includes an MR1-1 table 206 and an MR resolution rule set (RRS) 230. Table 206 includes an MR column 208, an MR rule set (MRRS) column 210 and an ARS column 212. Column 208 lists all MRs which may modify DR-1. For example, where DR-1 is "ECG", MR1-1A may be "previous", MR1-1B may be "admission", MR1-1C may be "report" and so on. In column 208, different MR1-1s are identified by distinct capital letters (e.g., A, B, etc.) following the reference MR1-1. Similar referencing distinguishes MRRSs and ARSs in columns 210 and 212, respectively.

Column 210 lists a separate MRRS corresponding to each MR in column 208. For example, where MR1-1A is "previous", MRRS1-1A may indicate that, for MR1-1A to modify DR-1, the term "previous" must appear within five words before or after DR-1 within the examined document. Other MRRSs are contemplated including MRRSs which include natural language processing and like functions.

ARS column 212 lists a separate ARS which are like the ARSs in FIG. 4, a separate ARS corresponding to each MR in column 208. For example, ARS1-1A corresponds to MR1-1A and indicates an address format for the DR/MR combination DR-1/MR1-1A.

Where a system supports DR/MR combinations, the above described linking process is a bit more complex. To this end, when a DR is identified by processor 14, processor 14 next attempts to determine if an MR corresponding to the DR and which meets the criteria required by the corresponding MRRS is present in the record being searched. Thus, for example, when processor 14 identifies DR-1, processor accesses table 200, identifies specification 204 (see FIG. 6) and searches for each MR in column 208 (see FIG. 7) according to corresponding MRRSs in column 210. When an MR which meets the criteria set forth in a corresponding MRRS is identified, processor 14 retrieves the ARS corresponding thereto and proceeds to construct an address corresponding to the DR/MR combination. Thereafter system supported linking is performed.

Figure 8:
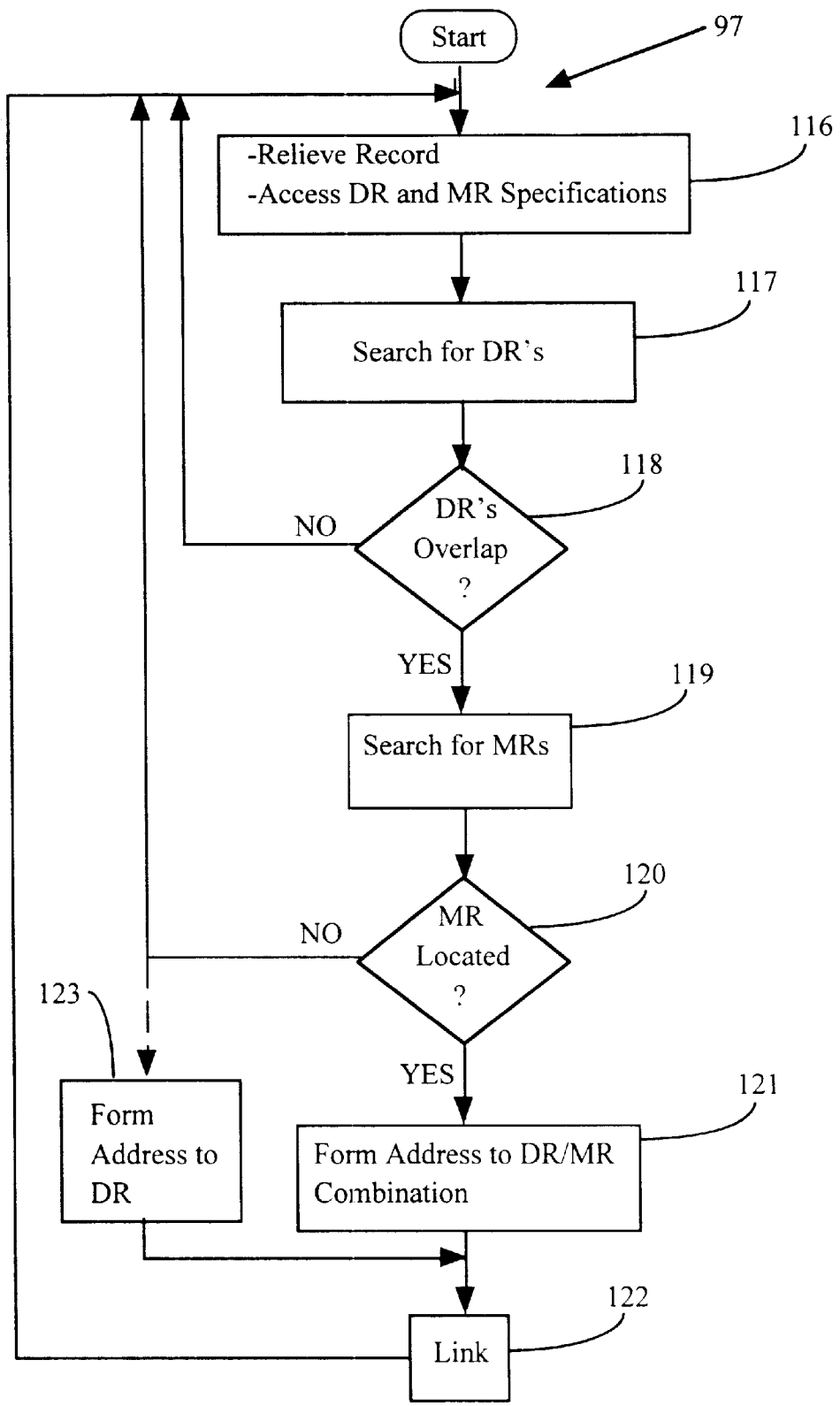
FIG. 8 is a flowchart illustrating a method for identifying DR/MR combinations in a record and forming an address corresponding thereto.

An exemplary DR/MR selection process 97 is illustrated in FIG. 8. Referring also to FIGS. 2, 6 and 7, at block 116 processor 14 receives a record and accesses DR and MR specifications 200, 204, respectively. At block 117 processor 14 searches for DRs and, if no DRs are located, loops back at block 118 until a DR is located. At block 119, after a DR is located, processor 14 searches for each MR in column 208 which may modify the located DR. If no modifying MR is located at block 120, control loops back to block 117. At block 120, when an MR which meets MRRS criteria is located, control passes to block 121 where an address corresponding to the DR/MR combination is formed. Linking again occurs at block 122 and control passes to block 117 to search for another DR.

Systems are also contemplated which support both DRs and DR/MR combinations. For example, where DR-1 is term "ECG" and MR1-1A is term "previous", a specification like specification 4 in FIG. 3 and a specification like specification 200 in FIG. 6 may both be supported. In this case, where DR-1 is identified in a record and MR1-1A is not identified, a link to the record or segment associated with DR-1 may still be made. Similarly, when the DR-1/MR1-1A combination is identified, a link to the record or segment associated therewith can be made. In FIG. 8, this alternate embodiment is represented by block 123 where, after a DR is identified and no MR is located, instead of looping back to block 117 to search for another DR, processor 14 forms an address corresponding only to the DR prior to linking at block 122. Unfortunately, as in the case where a long DR may include a short DR and additional text, here the DR/MR combination includes the base DR and ambiguity may result.

Therefore, as in the case of multiple length DRs, here, RRS 230 imposes a rule which specifies which of two DR/MR combinations or which of a DR/MR combination and a DR should be selected instead of the other when one combination includes the other and additional text. In this regard, the term "specifying reference" (SR) is used to refer generically to each of a DR and a DR/MR combination. The preferred rule is that the longest SR chosen. Once again, the manner in which the longer of two SRs is chosen is irrelevant and many different methods are contemplated.

In addition to the problem of dealing with SRs wherein a long SR includes a short SR and additional text, as with DRs, SRs may overlap and cause confusion. This is particularly true as MRRSs typically will specify, among other things, a range of terms about a corresponding DR which should be examined to identify an MR. Thus, where typical ranges are five terms before and after, the likelihood of overlap may be relatively high.

In this case it is contemplated that RRS 230 also includes rules for eliminating uncertainty when two SRs overlap. A preferred RRS 230 specifies that when a SR is identified, MRRSs corresponding to possible subsequent DR/MR combinations are modified such that the MRRS ranges are limited by the DR or MR in the identified SR and which is adjacent the subsequent possible combination. For example, assume a first combination including the MR "report" within two terms of the DR "ECG", a second DR/MR combination includes the MR "post-op" within five terms of the DR "X-ray image" and a record segment includes the phrase "The ECG post-op report and the X-ray image". In this case, when processor 14 considers the phrase, processor 14 first recognizes the "ECG report" DR/MR combination and forms an address therefore for linking purposes.

Thereafter, processor 14 accesses specification 200 (see FIG. 6), recognizes DR "X-ray image" in the record being searched, accesses the MR specification 204 associated with DR "X-ray image" and, for each MR in column 206, prior to searching for the MR, modifies the MRRS search range associated therewith as a function of the "ECG report" DR/MR combination if necessary. In the present case, because DR "X-ray image" is within three terms (i.e., "report and the X-ray image") of MR "report", the MRRS range preceding DR "X-ray image" is reduced from five terms to two terms. Thus, in this case, the DR/MR combination "post-op X-ray image" is not identified despite due to formation of the "ECG report" combination.

Another problem which may arise may be that a single DR instance may possibly be included in two overlapping DR/MR combinations. For example, the DR "ECG" may be modifiable by both MRs "report" and "admission" and a phrase "admission ECG report" may appear in a record. In this case which of two DR/MR combinations should be selected for linking may cause confusion. Here, as in the case of overlapping DRs, RRS 230 includes a rule which causes the first of two DR/MR combinations to be selected when a single DR instance is included in overlapping combinations.

Yet one other problem is that, in some cases, it might be desirable to have a single MR modify two DRs and in that case, each of two DR/MR combinations, although overlapping, should be linked to corresponding records and selectable by a system user. For example, assume a record includes the phrase "See the ECG image and x-ray image of Jan. 15, 1996 . . . " where "ECG image" and "X-ray image" are each DRs and date "Jan. 15, 1996" is an MR which may modify each of the two DRs.

In this case, MR "Jan. 16, 1996" may be meant to modify only "X-ray image" or both "X-ray image" and "ECG image." An ambiguous situation occurs. Among others, the present invention contemplates three general solutions for dealing with such ambiguity.

Figure 25:
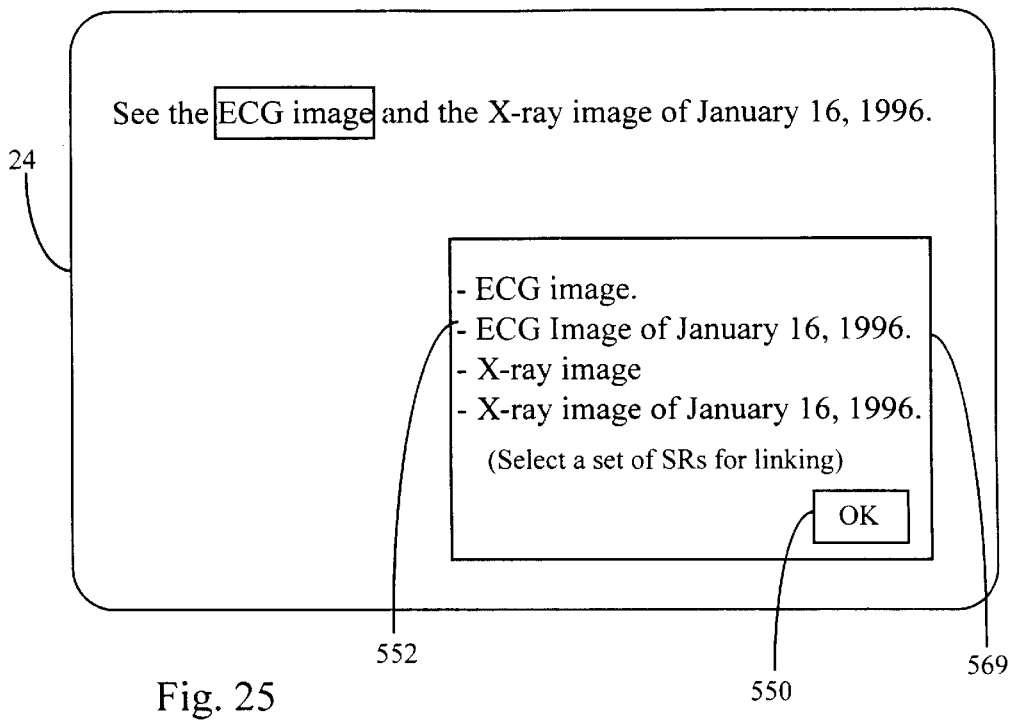
FIG. 25 is a schematic diagram illustrating an SR choice box according to the present invention.

First, where ambiguity occurs, processor 14 may query a system user to determine which, if any, DR/MR combinations and which DRs should be used for linking purposes. In the present example, this is accomplished by, when a system recognizes potentially overlapping SRs, providing a selection box to the user indicating all possible SRs (i.e., DRs or DR/MR combinations) associated with a phrase. Referring to FIG. 25, box 550 indicates four possible SRs including "ECG image".

"ECG image of Jan. 16, 1996", "x-ray image" and "x-ray image of Jan. 16, 1996." In addition an "OK" icon 569 is provided. After highlighting a set (e.g., two of them, all of them, none of them, etc.) of SRs to be formed when OK icon 569 is selected, addresses corresponding to all selected SRs are formed and links are made. Where selected SRs overlap, upon subsequently selecting an overlapping SR, a subsequent choice step is supported by processor 14 as described in more detail below.

Second, where ambiguity occurs, processor 14 may automatically identify every possible SR combination generating addresses for each and forming links for each. Thus, in FIG. 25, a separate link to each of the four SRs listed would automatically be formed without providing an option to a system user. In this regard, processor 14 may, when an SR is identified, form an address to a corresponding record and, prior to forming a link for subsequent selection purposes, determine if a corresponding record actually exists. Where a record does not exist, the link is foregone.

After links are formed and when a record including highlighted SRs is presented to a user, upon designation of an overlapping SR, processor 14 provides a choice box for a user. Herein the term "designate" is used to refer to a process whereby a system user may point to text on a display screen (e.g., via a mouse controlled cursor) without actually taking an affirmative step to select the text. This action is also referred to in the industry as "hovering over" an icon or object. For example, a user may place a pointing arrow icon on an SR without selecting the SR.

Figure 26:
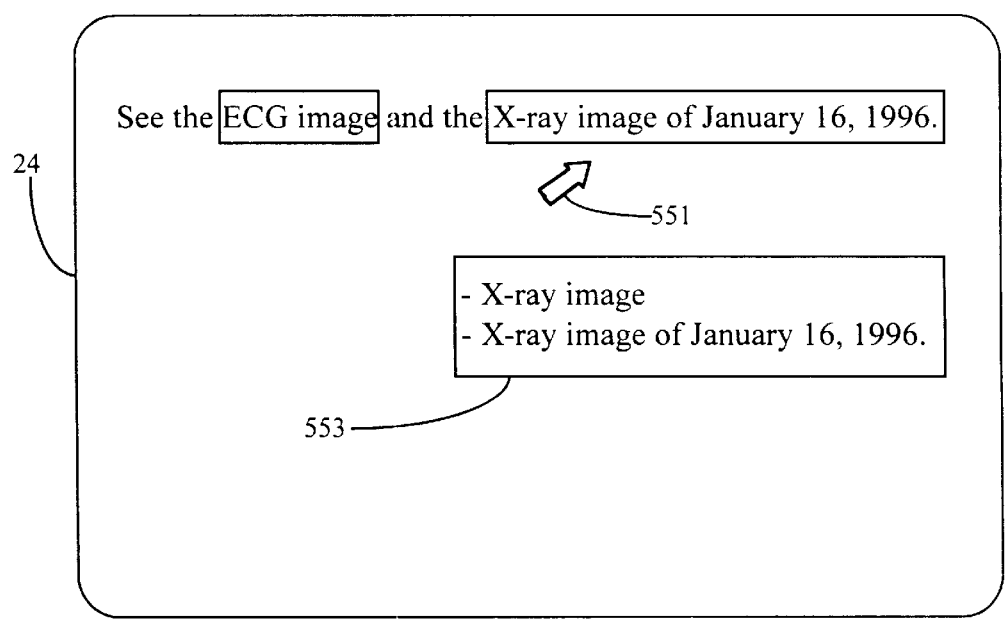
FIG. 26 is a schematic diagram illustrating another choice box according to the present invention.

Referring to FIG. 26, boxed text indicates highlighted text corresponding to one ore more SRs. Assuming each of "X-ray image" and "X-ray image of Jan. 16, 1996" are overlapping SRs which correspond to different records, when the phrase "X-ray image" is designated via a mouse controlled cursor 551 or the like, processor 14 automatically provides a selection box 553 including a list of possible SRs for linking. In this case the list includes "X-ray image" and "X-ray image of Jan. 16, 1996." One list SR can be selected via appropriate mouse activation to form a desired link.

Third, when ambiguity occurs, processor 14 may be provided with intelligence which enables processor 14 to determine which of several different SRs should be supported by addressing and linking capabilities. For example, in one embodiment, as above, the general rule that the longest of two possible SRs should be supported and the shorter discarded is assumed. In another embodiment, it is assumed that where two or more DRs appear in an inclusive (i.e., the last and second last DRs in the list are separated by the word "and") or an exclusive (i.e., the last and second last DRs in the list are separated by the word "or") list and the last DR in the list is modified by an MR which follows the last DR, each of the DRs in the list should be modified by the MR independent of whether or not the MR meets the MRRS requirements for a specific DR. For instance, in the present example where a date MR may modify each of DRs "ECG image" and "X-ray image" but date "Jan. 16, 1996" is separated from phrase "ECG image" by terms which place the date outside the MRRS range for phrase "ECG image," because phrases "ECG image" and "X-ray image" are separated by term "and" and date MR "Jan. 16, 1996" follows DR "X-ray image" and modifies "X-ray image," it would be assumed DR "ECG image" is also meant to be modified by the date MR (i.e., "Jan. 16, 1996").

It is contemplated that processor 14 would support many other rules such as what to do when an MR precedes one DR in a list of DRs or what to do when an MR precedes a DR list and so on. In addition, it is contemplated that combinations of each of the three approaches above, may also be supported. For example, in some cases processor 14 may be programmed to automatically select one of several different SRs, in other cases processor 14 may be programmed to automatically form all possible SR addresses and links while in other cases processor 14 may be programmed to provide SR options to a system user. Moreover, other lists which are neither inclusive nor exclusive may be recognized by the processor which may distribute the effect of a proximate MR to each DR in such a list.

Figure 27A:
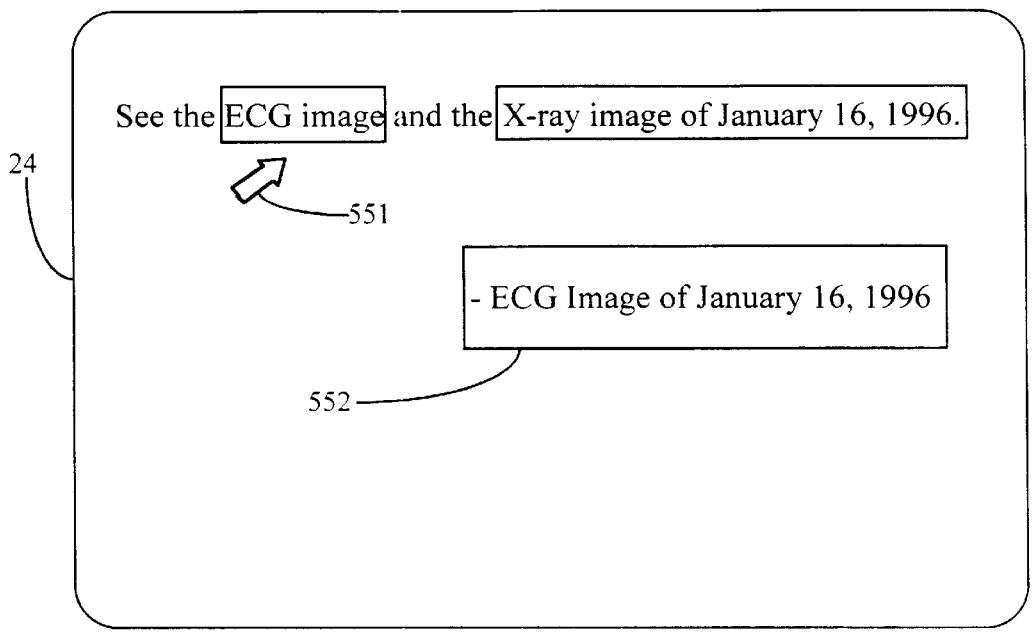
Figure 27B:
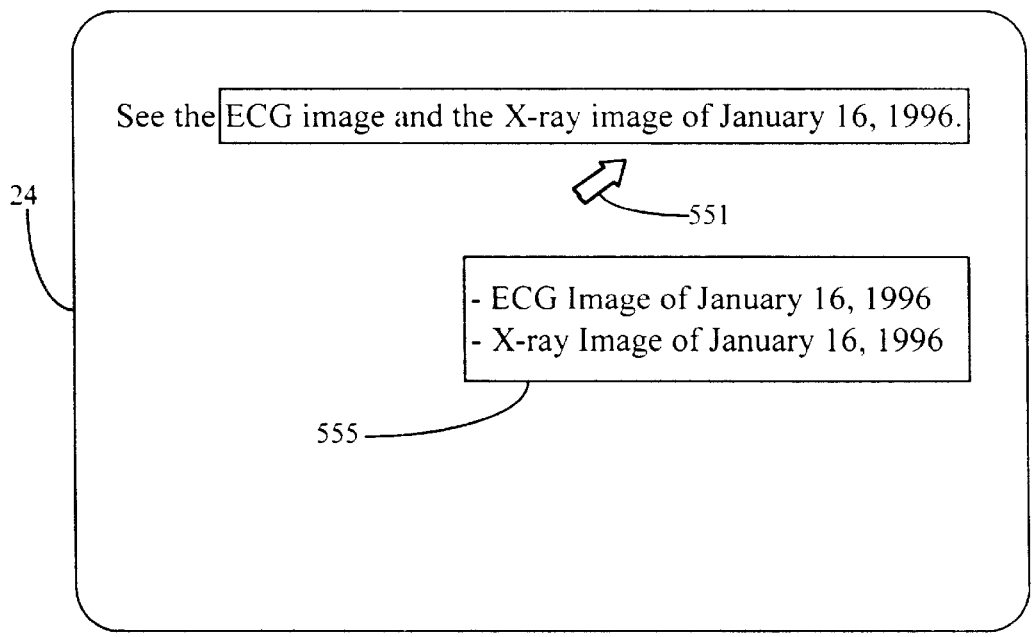
FIG. 27b illustrates a choice box.

When SRs overlap (e.g., one MR modified each of two DRs) and are displayed, a tool must be provided to enable a user to separately select each SR from a record despite the overlap. To this end, referring to FIG. 27a, the exemplary phrase "See the ECG image and X-ray image of Jan. 16, 1996 . . . " is illustrated as it would appear in one embodiment of the invention after highlighting and linking. In FIGS. 27a–27b, a box around text indicates highlighting. Thus, in FIG. 27a phrases "ECG image" and "X-ray image of Jan. 16, 1996" are both highlighted. In this instance, it is assumed date "Jan. 16, 1996" modifies each of phrases "ECG image" and "X-ray image." Nevertheless, because the phrase "ECG image" is separated from MR "Jan. 16, 1996," as illustrated, a record observer would not recognize the modifying relationship.

Here, when a mouse controlled cursor 551 is used to designate a DR which is separated from an associated MR, processor 14 provides an SR description box 552 to help the user navigate system records. For example, referring still to FIG. 27a, when phrase "ECG image" is pointed to prior to selection thereof, processor 14 provides description box 552 adjacent phrase "ECG image" showing the SR (i.e., "ECG image of Jan. 16, 1996"). Thereafter, selection via a mouse or the like links the user to the corresponding ECG image of Jan. 16, 1996.

As another example, when two DRs are separated by the word "and" and one of the DRs is modified by an MR such that it will be assumed both DRs are to modified by the MR, processor 14 may be programmed to highlight the entire inclusive phrase "ECG image and X-ray image of Jan. 16, 1996" as illustrated in FIG. 27b. In this case, when a mouse controlled pointing icon 551 is used to designate any part of the highlighted phrase, a selection box 555 opens which lists all possible DR/MR combinations in the phrase. In this case the possible combinations include "ECG image of Jan. 16, 1996" and "X-ray image of Jan. 16, 1996." Thereafter, activation of an appropriate mouse button causes combination selection and linking as described above.

The invention also contemplates a system which supports various MR levels such that one or more MRs can be further qualified or modified by another MR in another MR level. Thus, for example, where DR-1 is "ECG" and MR1-1A is "previous", a second level MR, MR2-1A, may be "record" while another second level MR, MR2-1B, may be "heartbeat". In this case when a DR/MR1-1A combination is identified, processor 14 searches a range of terms adjacent MR1-1A to identify one of the second level MRs (i.e., MR2-1A, MR2-1B, etc).

To support this type of system the DR specification would be essentially identical to the specification of FIG. 6. However, the MR specification would be different than the specification of FIG. 7. Referring to FIG. 9, an MR1-1 specification 240 which supports two MR levels is illustrated. Specification 240 includes an MR table 242 including an MR1-1 column 244, an MRRS1-1 column 245 and an MR2 specification column 246. Column 244 includes a list of all MRs which may modify DR-1 (see FIG. 6).

Column 245 includes a list at separate MRRSs corresponding to each MR1-1 in column 242. For example, where MR1-1A is "previous", MRRS1-1A may indicate that, for MR1-1A to modify DR-1, the term "previous" must appear within five words before or after DR-1 within the examined document. Other MRRSs are contemplated including MRRSs which include natural language processing and like functions.

In addition, the MRRS range may be any range including a text fragment, a sentence segment in which a DR appears, a sentence in which a DR appears, a paragraph in which a DR appears, a table cell in which a DR appears or an entire record (e.g. a patient ID# which appears once at the top of a record may modify every DR in the record).

Column 246 includes a separate MR2 specification for each MR1-1 in column 242. An exemplary MR2 specification is identified by numeral 250. Referring also to FIG. 10, specification 250 includes an MR table 252 and an M2 resolution rule set (RRS) 254. Table 250 includes an MR2-1 column 256, an MRRS2-1 column 258 and an ARS2-1 column 260. Referring to FIGS. 9 and 10, column 256 lists all MR2-1s which may modify MR1-1A. For example, where DR-1 is "ECG" and MR1-1A is "previous", MR2-1A may be "report".

Column 258 lists a separate MRRS corresponding to each MR2-1 in column 256. For example, where MR2-1A is "report", MRRS2-1A may indicate that, for MR2-1A to modify MR1-1A, the term "report" must appear within five words before or after MR1-1A within the examined document provided intervening words are not syntactically relevant or bring up new subject matter.

ARS2-1 column 260 lists ARSs which are like the ARSs in FIG. 4, a separate ARS corresponding to each MR2-1 in column 256. For example, ARS2-1A corresponds to MR2-1A and indicates an address format for the DR/MR combination DR-1/MR1-1A/MR2-1A.

Where a system supports DR/MR1/MR2 combinations, the above described linking process is more complex. To this end, when a DR is identified by processor 14, processor 14 next attempts to determine if an MR1 corresponding to the DR and which meets the criteria set forth in the corresponding MRRS1 is present in the record being searched. Thus, for example, when processor 14 identifies DR-1, processor accesses table 200 (see FIG. 6) and table 242 (see FIG. 9), identifies specification 240 and searches for each MR1-1 in column 244 according to corresponding MRRS1-1s in column 245.

When an MR1-1 which meets the criteria set forth in a corresponding MRRS1-1 is identified, processor 14 accesses the MR2-1 specification associated with the identified MR1-1. In the present case it is assumed MR1-1A is identified and therefore processor 14 accesses specification 250 (see FIG. 10). Next, processor 14 attempts to determine if an MR2-1 corresponding to MR1-1A and which meets the criteria set forth in the corresponding MRRS2-1 is present in the record being searched. Thus, for example, when processor 14 identifies MR1-1A, processor 14 accesses specification 250, accesses table 252 and searches for each MR2-1 in column 256 according to corresponding MRRS2-1s in column 258. When an MR2-1 meets the criteria set out in a corresponding MRRS2-1, processor 14 accesses an associated ARS2-1 in column 260 and proceeds to form an address to the DR-1/MR1/MR2 combination which is consistent with the address format specified by the ARS.

As in the cases of SRs which overlap or form parts of other SRs, where there are two or more MR levels, confusion due to overlap and common DRs and MRs among combinations result. Therefore, it is contemplated that RRS 254 includes rules which eliminate ambiguity when overlap and common terms occur. To this end, as in the other examples above, the preferred rules specify that when one SR is longer than another, the longer combination is selected and the shorter combination is discarded. In this regard, where a first SR is longer than a second and includes the second, processor 14 identifies the longer SR for linking purposes.

In addition, when one MRRS range searched extends into a previously identified DR/MR combination, the MRRS range corresponding to the one MRRS is restricted to terms which do not include the previously identified combination and when two combinations overlap the first is identified and the second is discarded.

While preferred resolution rule sets have been described above, the broadest aspect of the rule limitations is that at least some rules are provided to eliminate ambiguity in selecting DRs and DR/MR combinations for linking purposes. For example, many other resolution rule sets are contemplated. For instance, according to another limited resolution rule instead of identifying a first DR and discarding the second, where two DRs overlap, the second of two DRs could be selected and the first discarded. Similarly, instead of having a rule which always causes processor 14 to identify the longest SR at the expense of other SRs, the RRSs may specify exceptions. For example, where a first DR includes the phrase "admission ECG report" which may be modified by the MR "image" within three terms (i.e., the MRRS corresponding to MR "image" specifies a range of three terms before and after the DR), a second DR includes the term "X-ray" which may also be modified by the MR "image" within three terms and a record segment includes the phrase "Upon a perusal of the admission ECG report, X-ray image, and examination notes . . . ", if processor 14 always selected the longest SR and disregarded the rest the identified SRs would be "admission ECG report image" and "X-ray". The combination "X-ray image" would be discarded.

Instead, an exception may be to limit an MRRS search range by a second DR if a first DR is identified and the second DR appears between the first DR and an MR. In this case, the term "X-ray" would limit processor 14 examination range to locate MR "image" and the result would be two linking references including "admission ECG report" and "X-ray image", an outcome which is more likely to be intended. A rule similar to this rule may also be included as an exception where a noun falls between a DR and a possible MR where the noun is not a DR. For example, in the phrase "ECG and ultrasound image" where "ECG" is a DR, "image" is an MR and ultrasound is not a DR, the term "ultrasound" should still delink the DR and MR such that the SR "ECG image" is not recognized.

In addition, the invention contemplates a "null" link wherein a DR such as "ultrasound" above may be defined without a corresponding address so that, while the DR is recognized, no link is formed. This feature enables an MR and another DR which are separated by the "ultrasound" DR to still be recognized as related. For instance, in the example above "ultrasound" may correspond to a null link such that when the phrase "ECG and ultrasound image" is identified, each of ECG and ultrasound are modified by the "image" MR, an "ECG image" link to an address is formed and a null address is linked to "ultrasound image".

One other preferred rule is that, when an SR is selected for address and linking purposes, the process of searching the record for additional SRs is limited by the previously selected SR. For example, where the phrase "previous ECG image and the X-ray image . . . " is encountered, processor 14 selects the phrase "previous ECG image" as a first SR and thereafter limits SR searches such that the searches do not include the selected phrase. Hence, the term "previous" will not, in this example, be considered a possible MR for modifying DR "X-ray image."

Another preferred rule is that when one MR may be included in two SRs, processor 14 should identify the SR including the DR which is closest to the MR for linking purposes and should select the related SR to form an address.

It should be appreciated that while the inventive methods are described or including first searching for DRs and then for MRs, the invention also contemplates systems wherein an MR may be sought first and a DR thereafter.

2. Creating Links Using a Table and Resolution Rules

While the ARSs described above are extremely useful, it has been recognized that other simpler tools can be used to form links between DRs in one record and other records referenced and associated with those DRs. To this end, the '177 reference teaches one system wherein specific DRs can be linked to specific records or record segments which are stored at known addresses. When a DR is assigned to a segment, the DR is correlated with the segment address and the DR and address are stored in a lookup table. Thereafter, during a linking procedure, a processor accesses the lookup table and searches a record for each DR in the table. When a DR is located, the processor links the DR in the record to the record at the corresponding address.

It has also been recognized that pre-existing DR/address tables may be used for linking purposes. Referring now to FIG. 11, an exemplary DR/address lookup table 270 is illustrated. Table 270 is comprised of two columns including a DR column 272 and an address column 274.

Column 272 includes a list of DRs. Column 274 includes a separate address for each DR in column 272. While it is contemplated that virtually any record may be addressed in column 274 and associated with a DR in column 272, in most cases the records associated with addresses in column 274 will be of a generic or semi-generic nature. For example, in the context of a medical facility, records associated with addresses in column 274 may be tutorials or informational bulletins. For instance, DR 276 is "ECG procedure" and the corresponding address 278 is the address of a bulletin which can be consulted to learn about an ECG procedure at the medical facility. As another example, DR 280 is "breast cancer bulletin" and the corresponding address 282 is the address of a bulletin which can be consulted to learn about recent developments in breast cancer research.

In operation, assuming the link creating processing feature is activated. As a physician enters information into a record, when the physician types in the phrase "breast cancer bulletin", the processor matches DR 280 to the typed phrase, identifies address 282 and forms a link between the DR in the record and the record indicated by address 282.

As in the case of systems which support ARSs, in systems which include DR/address tables, additional complexity is contemplated wherein DRs can be modified by one or more levels of MRs such that several different DR/MR combination levels may be supported. Extension of the DR/MR principles taught above should be easy for one of ordinary skill in the art.

In addition, it is contemplated that one SR may include or overlap another SR. In an including or overlapping situation, as in systems which support ARSs, it is contemplated that rules are provided which enable unambiguous selection of one SR and different treatment of the other. As above, the different treatment may constitute disregarding the other DR or combination or, in the case of a DR/MR combination, may constitute modifying an MRRS search range as a function of overlapping DRs and MRs.

3. Tag Enabling

While automatic address linking features described above are extremely useful, unless specific information within a record is separately addressable via conventional addressing protocols, such features do not facilitate recognition of specific information in a record after the record has been retrieved. For example, assuming each patient post-op record includes an abstract indicating the general nature of a surgery and the perceived outcome, if a physician wishes to view a record abstract, with conventional address linking systems, the physician has to provide the record address and, when the record is retrieved, then has to independently review the record to identify the abstract. While this may not be extremely burdensome in the case of an abstract which would likely have a known position (e.g., near the front or rear) within a record, other information types would likely be much more difficult to locate. In addition, where the physician must locate many (e.g., 10) different segments of information in a record, the task of manually locating information may prove daunting.

According to the present invention the concept of automatic linking is taken one step further and includes a system which automatically provides "tags" within records which can be used by processing applications to distinguish different information types within the record. To this end, generally, processor 14 is equipped to recognize characteristic sets which correspond to different record segments and, when a specific segment is identified, can place tags around the segment which are recognizable by other applications. Preferred tags are XML tags although any other tags which are recognized by a suitable application may be used and are certainly contemplated. Referring to FIGS. 2 and 12, database 2 may include an XML specification 290 including at least an XML rule set (XMLRS) column 292, an XML begin tag column 294 and an XML end tag column 296. A fourth column, an XML type column 298, is illustrated to simplify this explanation but may not be required in an actual system.

XML type column 298 lists all information types which XML specification 290 supports and indicates the types via descriptive names. For example, in the case of a medical facility, column 298 may include a patient ID type 300, heart rate type 302, image type 304, abstract type 306, diagnosis type 308, prescription type 310, etc.

Column 292 includes a separate XMLRS for each XML type listed in column 298. The XMLRSs provide rules to be used by processor 14 to determine if information within a record segment is of the corresponding XML type. For example, in the case of XML type patient ID 300, referring also to FIG. 13, XMLRS 312 includes a variable character string 314 which has a form recognizable as a patient ID. In the present case it is assumed that each patient at a medical facility is identified by an unambiguous and distinct character string including two numbers followed by two letters which are in turn followed by five numbers. In XMLRS 314 a "#" character indicates a digit from 0 through 9 while an "X" character indicates a letter. The first two characters are reserved for a year indication (e.g., 99 for 1999, etc.) The third and fourth characters are reserved for first and last name initials (e.g., Mary Jones would be M J). The final five characters indicate a unique consecutively assigned number provided via an admit, discharge, transfer (ADT) system (not illustrated) when a patient is admitted to the facility. In this case the ADT system begins with a "00001" number at the beginning of a new year and it is assumed that the facility admits less than 100,000 patients each year.

Figure 14:
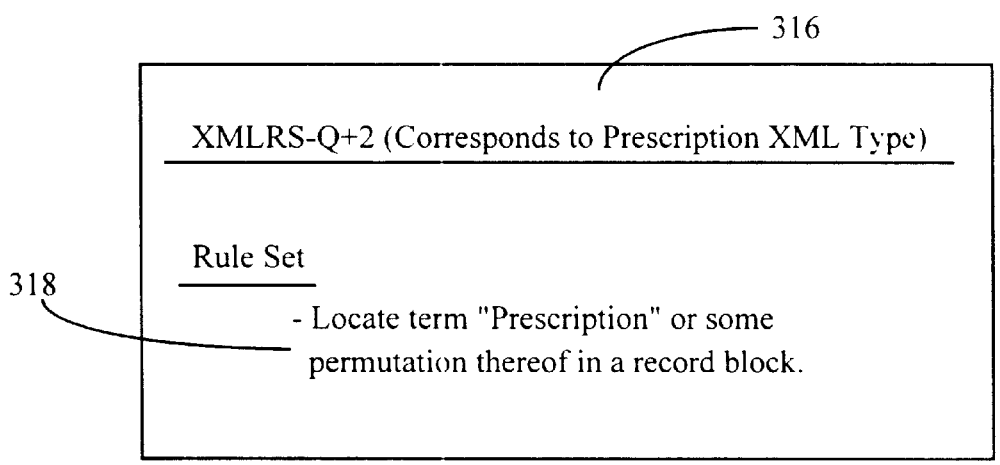
FIG. 14 is a schematic diagram of another exemplary XML rule set XMLRS-Q+2 of FIG. 12.

As another example, referring to FIGS. 12 and 14, an XMLRS 316 corresponding to the prescription XML type 310 is illustrated. In this case, it is presumed that the medical facility has many different electronic forms which may be used to prescribe a medication or a procedure and that each form has a different format including several information blocks. For example, a first form may include a block for prescription indication at the top of the form while a second form includes a block for prescription indication at the bottom of the form. It is also presumed that a generic form enables the physician to indicate a prescription in any of several different form blocks. For instance, the generic form may include five blocks and the physician may select any of the five different blocks for indicating a prescription, other examination information being provided in one or all of the additional four blocks. Furthermore, it is presumed that in any case where a prescription is ordered, the physician must use (i.e., type in) the term "prescription" in conjunction with the prescription.

In this case XMLRS 316 (i.e., KMLRS-Q+2) includes the rule that, to identify a prescription, processor 14 must locate the term "prescription" within a form block. When the term "prescription" is identified, the processor 14 recognizes the information with the block as a prescription, the prescription beginning at the beginning of the block and the prescription ending at the end of the block.

Referring again to FIG. 12, column 294 includes a begin tag BT corresponding to each XML type listed in column 298 which can be inserted into a record to indicate the beginning of information of the type in column 298. For example, tag BT-1 corresponding to XML type 300 (i.e., patient ID) may be "<patient ID>" while tag BT-2 corresponding the XML type 302 (i.e. heart rate) may be "<heart rate>".

Column 296 includes an end tag ET corresponding to each XML type listed in column 298 which can be inserted into a record to indicate the end of information of the type in column 298. For example, tag ET-1 corresponding to XML type 300 (i.e., patient ID) may be "</patient ID>" while tag ET-2 corresponding the XML type 302 (i.e. heart rate) may be "</heart rate>".

Figure 13:
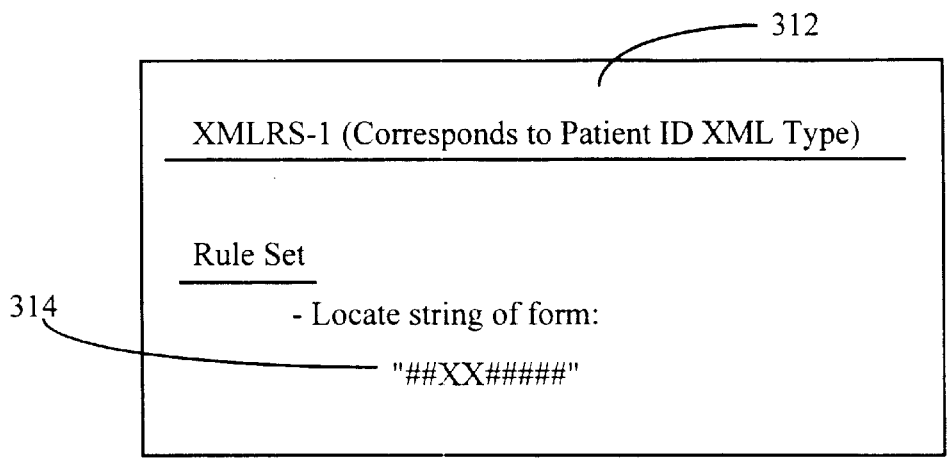
FIG. 13 is a schematic diagram of an exemplary XML rule set XMLS-1 of FIG. 12.
Figure 15:
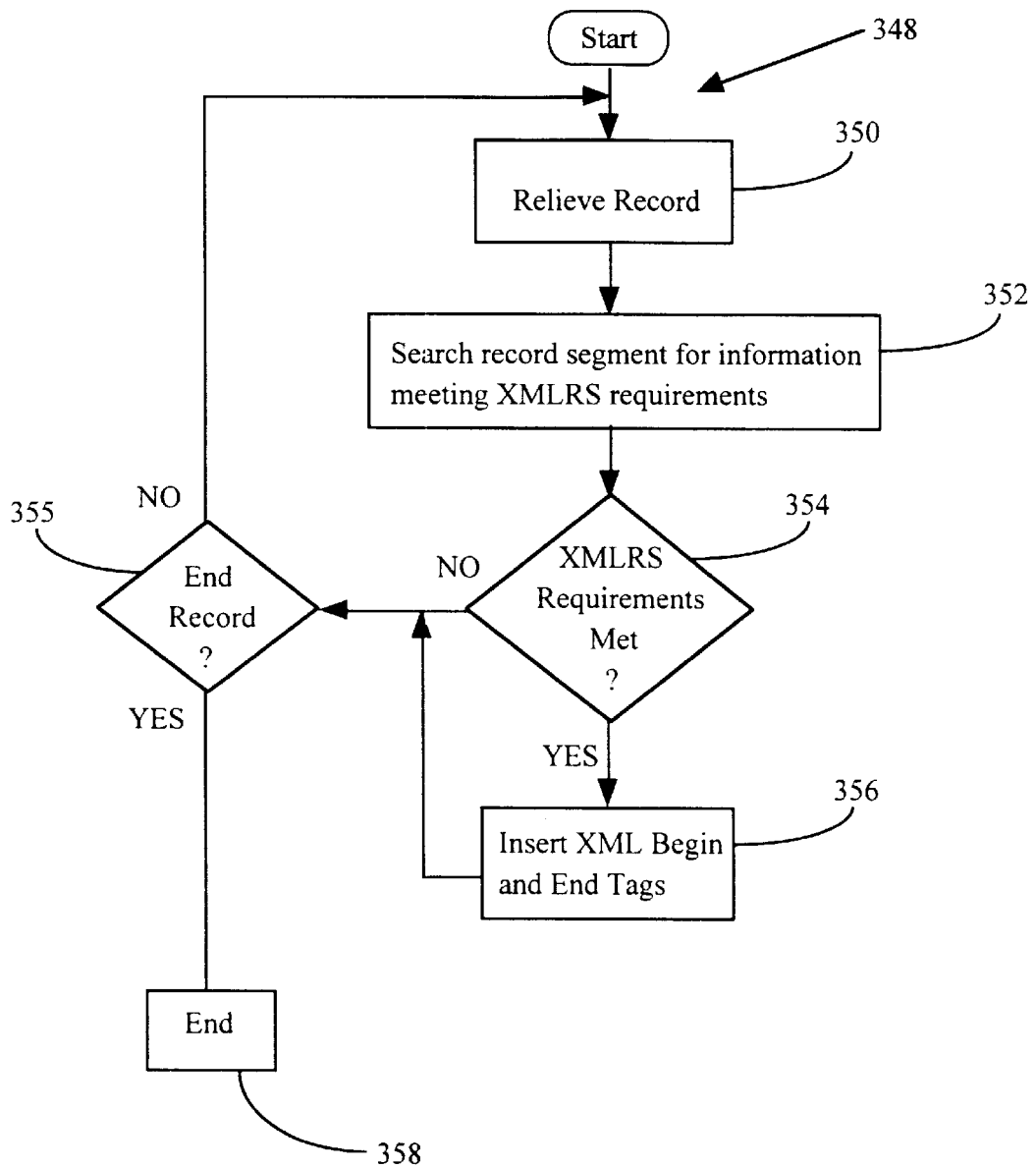
FIG. 15 is a flow chart illustrating an inventive method for identifying record segments for XML tagging.

Referring to FIG. 15, an exemplary XML enabling procedure 348 is illustrated. Referring also to FIG. 2, at process block 350 processor 14 receives a record. In this example, the record may be received in any of several different manners including batch downloading to processor 14 or, where a physician is entering a record via a word processor, by receiving record segments in real time. Referring also to FIGS. 12 through 14, as the record is received or after the record is received, at block 352, processor 14 searches the record segment by segment in accordance with the XMLRSs in column 292 to identify any information segments which meet the criteria specified in the XMLRSs.

At decision block 354, if no XMLRSs are satisfied by a currently examined segment, at decision block 355 processor 14 determines whether or not the previously examined segment is the last segment in the document and, if so, ends the XML searching function by proceeding to block 358. If there are additional record segments, processor 14 moves onto the next consecutive segment in the record by looping back to process block 352.

At process block 356, when an XMLRS is satisfied at block 354, processor 14 accesses corresponding begin and end tags in XML specification table 290 (see FIG. 12) and inserts corresponding XML begin and end tags into the record before and after the examined segment, respectively. Thus, in the present example, where a patient ID is identified, processor 14 inserts the begin tag patient ID <patient ID> and the end tag patient ID </patient ID> into the record before and after the identified ID, respectively. As known in the art, although inserted in the record, the XML tags are invisible to a record reader during normal record examination and are typically only recognized by a software application equipped to recognize and use XML tags.

After tags have been inserted in a record to distinguish one segment from others, processor 14 control passes to decision block 355 where processor 14 again determines if the previously examined segment was the last segment and, if the previously examined segment was the last segment, control passes to block 358. If the previously examined segment was not the last record segment control passes back up to process block 352 where the next segment is considered.

Once every record segment has been considered in light of the XMLRSs and all XML tags have been inserted into the record, the record is stored. At this point the record is tag enabled meaning that the record can be used by a tag enabled software application to identify specific information within the record. For example, where an application is searching for a record abstract associated with a patient report, after the report is accessed, the application simply searches for the XML tags corresponding to the beginning and the end of the abstract and accesses the information therebetween.

While the examples above include relatively simple XMLRSs in the context of a medical facility, more complex XMLRSs are contemplated and nested XMLs are also contemplated. For example, in the case of a United States patent specification, it is known that each patent generally includes several different sections or segments such as an abstract, a background, a summary, a brief description of drawings, a detailed description, a set of claims, figures and so on. It is also known that each patent segment is generally earmarked by a heading which indicates the information included in the segment and that each segment ends where the next segment begins. For example, the abstract is typically earmarked with the term "Abstract" or with the phrase "Abstract of the Invention" while the brief description of the drawings is typically earmarked with the phrase "Brief Description of the Drawings" and the claims are earmarked with the term "Claims".

Moreover, it is also known that within each main specification segment, other subsections are often readily identifiable via the form of the specification or the like. For instance, separate claims within the claims section of a specification begin with a number and end with a period while separate descriptions of figures within the brief description of the drawings begin with the term "FIG." or the term "FIGURE" and end with a period or a semicolon followed by another term "FIG." or "FIGURE" or by another major patent heading (e.g., "Detailed Description of the Invention". Furthermore, it is known that certain patent sections are typically preceded and followed by other specific specification sections. Thus, for example, the summary usually follows the background and precedes a brief description of drawings.

An exemplary XML specification 360 which supports nesting and which can be used to automatically render a patent specification tag enabled is illustrated in FIG. 16 and includes a type column 362, an XMLRS column 364 and begin and end tag columns 366 and 368, respectively. Structure and operation of specification 360 is similar to structure and operation of specification 290 (see FIG. 12) and therefore, in the interest of simplifying this explanation, only unique features of specification 360 will be described here in detail.

In FIG. 16 patent specification XML types are listed in column 362 including, among others, a "brief description of the drawings" type 370 and a "claims" type 372. A separate XMLRS (XMLRS-5, XMLRS-7) is listed for each of types 370 and 372, respectively. For example, referring also to FIG. 17, exemplary XMLRS-5 corresponding to the brief description of the drawings includes rules requiring processor 14 to search, after a "Summary of the Invention" section of the specification and before the "Detailed Description of the Invention" section to locate a heading including the phrase "Description of the Drawings" or some permutation thereof (i.e., "Brief Description of the Several Views of the Drawings" identified using natural language processing) followed by at least one description of a figure or drawing. Thus, each XMLRS may include many different contingencies. In fact, some requirements may be weighted such that more detailed intelligence is reflected within the decision making process.

Referring to FIG. 18, exemplary XMLRS-7 corresponding to the claims includes the rules requiring processor 14 to search an entire specification for a claims section by searching for a title "Claims" (or some permutation thereof) followed within ten terms by a number "1" with a single sentence thereafter ending with a period.

Referring again to FIG. 16, separate begin and end tags are listed for each of types 370 and 372 indicating tags to be inserted in a record when a corresponding XML type is identified.

In addition to supporting a first XML level which corresponds to major sections of a patent specification, specification 360 also supports a second XML level which divides major patent sections into even smaller record segments. Referring still to FIG. 16 first level XMLs correspond to XMLRSs in column 364 which include a single number thereafter (e.g., XMLRS-1, XMLRS-7, etc.) while second level XMLs correspond to XMLRSs in column 364 which include two numbers thereafter. In addition, to distinguish second from first level XMLRSs, second level XMLRSs are indented to the right in column 364. With respect to second level XMLRs, the first number following an XMLRS indicates the first level XML in which the second level XML is nested and the second number indicates a specific XMLRS nested under the corresponding first XML. For example, XMLRS-5-1 is nested within XMLRS-5 which corresponding to the "Brief Description of the Drawings" and therefore further breaks down the "Brief Description of the Drawings" record segment.

In the present example, XMLRS-5-1 includes rules to identify the description of the first figure described in the description of the drawings. To this end, referring to FIGS. 16 and 19 XMLRS-5-1 requires all of the XMLRS-5 rules to be met and, in addition, requires that a paragraph begin with the phrase "FIG. 1" or some permutation thereof, end in a period or a semi-colon and be followed by a paragraph which begins with the phrase "FIG. 2" or the title "Detailed Description" or some permutation thereof. In addition, rules for identifying the end of a segment are provided. For instance, although not illustrated, XMLRS-5-1 would indicate that the FIG. 1 segment ends at the beginning of another segment at the same XML level (i.e., "FIG. 2") or a higher level (i.e., a title such as "Detailed Description").

As another example, XMLRS-7-1 is nested within XMLRS-7 which corresponds to the "claims" XML and therefore further breaks down the "claims" record segment. Similarly, XMLRS-7-2 is nested within XMLRS-7 and therefore further breaks down the "claims" record segment. In the present example XMLRS-7-1 and XMLRS-7-2 include rules to identify claims 1 and 2 of the patent specification. To this end, referring to FIGS. 16 and 20, XMLRS-7-1 requires all of the rules of XMLRS-7 to be met and, in addition, requires that a paragraph including a single sentence begin with the number "1" end with a period and that the following paragraph begin with the number "2". Similarly, XMLRS-7-2 (not illustrated in detail) requires all of the rules of XMLRS-7 to be met and, in addition, requires that a paragraph begin with the number "2", including a single sentence and that the following paragraph begin with the number "3".

Figure 21:
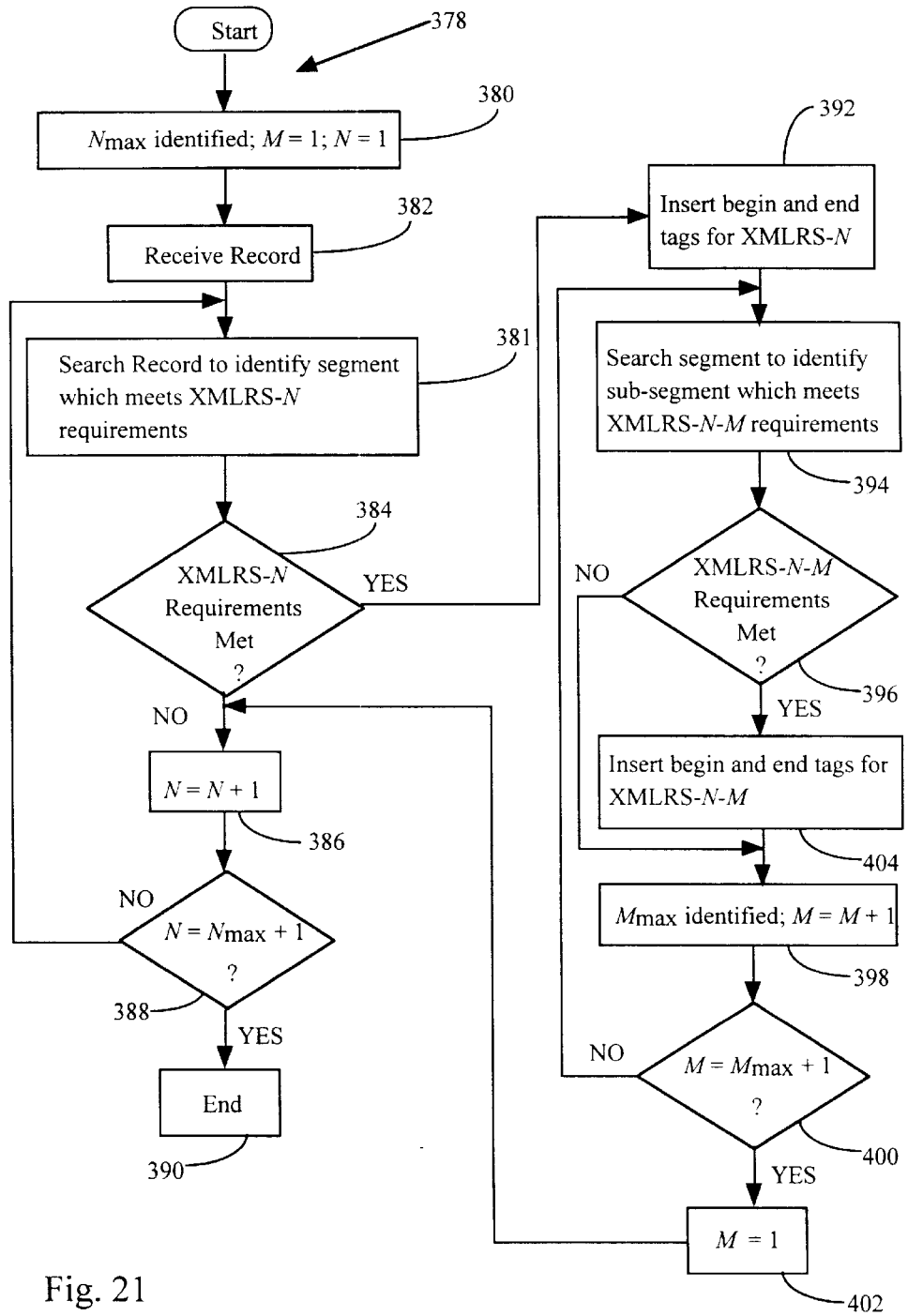
FIG. 21 is a flow chart illustrating an inventive method for supporting automatic XML tagging including nested XML tags.

Referring to FIG. 21, an exemplary XML enabling procedure 378 which supports two level XML nesting is illustrated. Referring also to FIGS. 2 and 16, initially it is assumed that processor 14 has access to XML specification 360 in database 2. At process block 380 processor 14 identifies the number N of first level XMLs in specification 360. In this case it is assumed N is 8. In addition, at block 382 processor 14 sets N and M counters equal to 1 where N represents a first level XML and M represents a second level XML.

At block 382 processor 14 receives a record. In this example the record is a patent specification and it will be assumed the specification is downloaded to processor 14 in batch form. After the record is received, at block 381 processor 14 searches the record to identify any information segments which meet the criteria specified in XMLRS-N. Here, because N is initially 1, the first rule set XMLRS-1 is used to search the record.

At decision block 384, if XMLRS-1 is not satisfied, control passes to block 386 where N is incremented by one. In the present example N is incremented to 2. At block 388 N is compared to Nmax to determine if segments corresponding to all of the XMLRSs have been sought. Where all of the segments have been sought control passes to block 390 and, to the extent possible, the record has been made XML ready. Referring still to block 388, in the present case, because Nmax is 8 and N is currently 2, control passes back up to block 381.

Referring still to FIG. 21 and specifically to block 384, where XMLRS-1 requirements are met at block 384, control passes to block 392 where begin and end XML tags associated with XMLRS-1 are inserted within the record to indicate the beginning and the end of the XML associated with XMLRS-1. Next, at block 394, processor 14 searches the segment between the XMLRS-1 begin and end tags to identify any sub-segments thereof which meet the XMLRS-N-M requirements. In this case, because N and M are both 1, the requirements searched correspond to the XMLRS-1-1 rules.

Where XMLRS-1-1 requirements are not met, at block 398 processor 14 identifies Mmax (i.e. the number of second level XMLs within first level XMLRS-1). In addition, at block 398 processor 14 increments flag M by one (i.e., in this case from 1 to 2). At block 400 processor 14 compares M to Mmax to determine if all of the XMLRS-1 second level XMLRSs have been considered. Where all of the second level XMLRSs corresponding to XMLRS-1 have not been considered, control loops back up to block 394 where processor 14 searches the segment for sub-segments which meet the criteria set out in XMLRS-1-2. Where all of the second level XMLRSs corresponding to XMLRS-1 have been considered, control passes to block 402 where M is reset to 1 prior to control passing back to block 386. At block 386 N is again incremented and hence the next XMLRS-N rule set is considered.

Continuing, referring again to block 396, where all of the XMLRS-1-1 requirements are met by a sub-segment of the segment between the XMLRS-1 begin and end tags, control passes to block 404 where processor 14 inserts the begin and end tags for XMLRS-1-1. Thereafter control passes back to block 398. The above process continues until N is equal to 9 at decision block 388 at which point control passes to block 390 and the record is, to the extent possible, XML ready.

Specifically, referring again to FIGS. 17 and 21 and block 386, when N is incremented to value 5 and control passes back to block 381, processor 14 applies the rules of XMLRS-5 to identify the description of the drawings section of the specification. When the description of the drawings is identified at block 384, control passes to block 392 and begin and end tags corresponding to the description of the drawings are inserted in the specification before and after the description of the drawings section.

Next control passes to block 394 and processor 14 searches the description of the drawings segment for a segment which meets the criteria of XMLRS-5-1 which indicates how to identify the description of the first figure described in the description of the drawings segment (see FIG. 19). Once the description of the first drawing is identified processor 14 inserts begin and end tags corresponding thereto before and after the segment at block 404. Control then passes through blocks 398 and 400 prior to being returned to block 394.

As another specific example, referring to block 384 in FIG. 21 and also to FIG. 18, when N is set equal to 7 and so that processor 14 is searching the record using XMLRS-7 to identify the claims segment of the specification, processor 14 applies the rules illustrated in FIG. 18. When the XMLRS-7 requirements are met, processor 14 inserts tags at block 392 and then searches between the tags to identify a claim 1 sub-segment at block 394 and as specified by XMLRS-7-1 (see FIG. 20). When claim 1 is identified at block 396, processor 14 inserts tags associated therewith at block 404 and returns control to block 398. Thereafter, to identify the claim 2 segment (assuming a second claim exists), processor 14 loops through blocks 398, 400, 394, 396 and 404 again.

Thus, process 378 causes processor 14 to methodically step through each XMLRS to identify record segments which meet XMLRS requirements and, when requirements are met, processor automatically inserts XML tags earmarking identified segments.

It should also be noted that while only one and two level nested XML schemes are described herein, the invention contemplates XML schemes which include many more than two levels and a processor and method which accommodate such schemes.

While one rule type is described above for determining where to place an end tag which is dependent upon the information within the segment to be indicated by the tags, another rule type depends on the location of the next start tag which is identified which is at the same or a higher tag level. For example, in the case of an exemplary patent, this rule type would require placement of an end claim 1 tag just prior to the beginning of an identified claim 2 or just prior to the beginning of some other data segment which is on the same tag level as claims (e.g., an abstract or the like).

One other aspect of the invention is that processor 14 may be equipped to, upon receiving a record, examine the record to identify information indicating which of several XML specification tables to use during the XML record readying process. To this end, it has been recognized that, even within a single facility or a single department within a facility, several different XML specifications may be required to categorize all of the information or different information types used by the processor. For example, in a medical facility there may be a first XML specification to be used with informational bulletins/brochures and there may be a second XML specification to be used to earmark information in patient examination reports. While each specification will include XMLRSs and tags which earmark specific information, the information to be earmarked may be different. For instance, the XMLRSs corresponding to a patient record may include patient ID, data, time, diagnosis, prescription, miscellaneous, etc, while the XMLRSs corresponding to brochures may include an introduction, publication date, symptoms, complications, treatments, additional contacts for follow-up, recommendations, etc.

Figure 22:
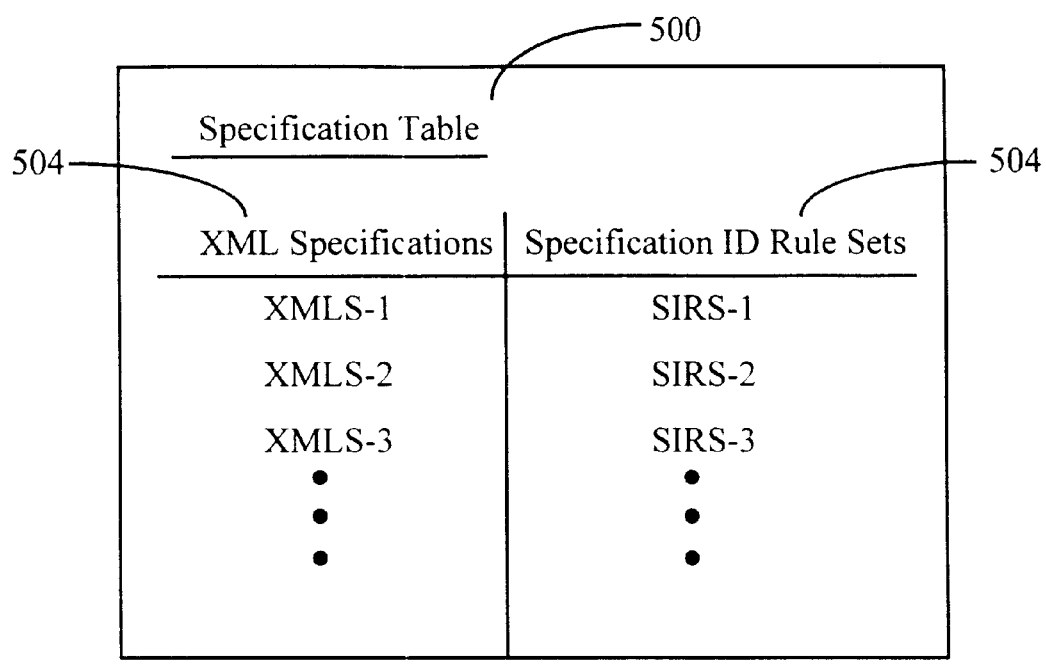
FIG. 22 is a specification table according to the present invention.

In this regard it is contemplated that, when a system supports more than one XML specification and a record is received for tag enabling (i.e., insertion of XML tags), processor 14 first examines the record to identify which XML specification to use during the tag enabling process. To accomplish this task, referring to FIGS. 2 and 22, a specification table 500 is stored on database 2. Table 500 includes a list of XML specifications supported by processor 14, table 500 including an XML specification (XMLS) list in a first column 502 and corresponding specification identification rule sets (SIRSs) in a second column 504. List 502 identifies each XMLS which is supported by processor 14. Each SIRS includes a list of rules which can be applied by processor 14 to examine a record and determine which of several different XMLSs to use during the XML readying process.

For example, in a medical facility which has had an electronic storage system for some time, it will be assumed that every patient examination record has been provided a unique record number having the form "########" where each "#" is a number between 0 and 9, the first two #'s correspond to the last two digits in a year (i.e., 99 indicates 1999) and the third through eighth #'s correspond to an intra-year unique examination. In addition consistent with the specification above, each patient is assigned an ID number having the form "##XX#####" which is included on the record. While all of the records have been stored electronically it is assumed none of the records currently includes XML tags. In this case, a SIRS corresponding to an XMLS which should be used with a patient record to tag enable the record requires that the record include a record number and a patient identification number.

Referring again to FIGS. 2 and 22, when processor 14 receives a record for XML readying, processor 14 accesses SIRSs in table 500 and applies the rules therein to the record. In the present case, when the record constitutes a patient examination, by applying the SIRS rules, processor 14 recognizes that the record is a patient record and selects the XMLS corresponding thereto for XML readying purposes. Thereafter the tag enabling process described above is carried out to tag enable the record.

In the alternative, when a record is received and is to be tag enabled (i.e., tags are to be inserted), instead of having processor 14 determine which of several XML specifications to use for tag enabling, processor 14 may provide a list of possible XML specifications and enable a user, via a selection device (e.g., a mouse controlled cursor), to select one of the XML specifications. Thereafter processor 14 uses the selected specification.

Because XML and similar tag types are often hidden from a system user's view and are only identifiable via a tag enabled application so as not to obscure reading of a record, there typically is no way for a system user to observe record tags to confirm existence and correctness. To facilitate confirmation, the present invention contemplates a tag indicating feature whereby, when selected, tag indicators appear in the record. For example, in a preferred embodiment, while observing a record via a display, by selecting a specific key sequence on a keyboard, processor 14 is instructed to indicate tags within the record. For instance, patent title tags may include "<title>" and "</title>" before and after the patent title, respectively. By selecting another specific key sequence the tag revealing feature may be turned off. Other functionality may also be supported such as facilitating elimination of one, all or a subset of tags from a record via a recognizable key sequence or perhaps inclusion of additional tags via a specific key sequence.

4. Tag Modification

The present invention also contemplates that records stored on a system may be altered after tags have been added to the record and that modifications to a record may affect whether or not tags originally inserted within the record should remain or should be removed or modified. In other words, modifications including deleting, copying, altering and moving may modify the characteristics of a segment such that the segment no longer meets the requirements of the characteristic set identified in an XMLRS. For this reason the present invention also includes a processor function whereby, when a tag enabled record is modified, the modifications are monitored and, if necessary, the tags are modified to reflect record modifications.

In its simplest form, when a tag enabled is modified the inventive function includes assuming the tags are all incorrect and removing all of the XML tags from the record. To this end, referring to FIGS. 2 and 23, processor 14 monitors record modifications at blocks 420 and 422. At block 422, when the record is modified processor 14 control passes to block 424 where all record tags are removed.

While this solution is drastic, this solution ensures that tag enabled applications do not reference incorrect information. In addition, it has been recognized that in many cases complete removal of tags is required for a system to operate properly. For example, where a system supports more than one XML specification, even a single modification to a record may render all of the XML tags incorrect as the modification may cause the record to no longer meet the requirements of the XML SIRS (see FIG. 22).

Figure 23:
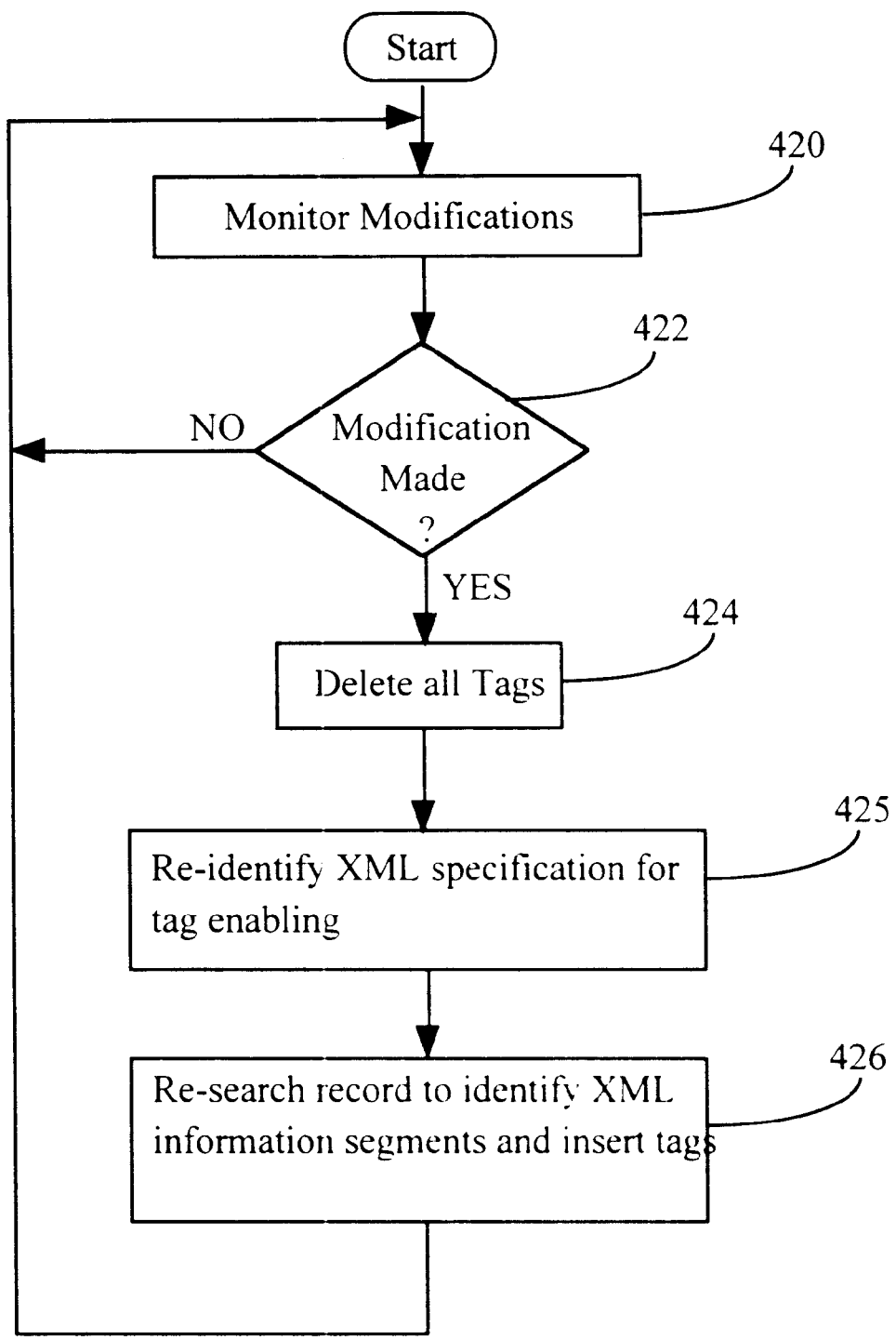
FIG. 23 is a flow chart illustrating a method for altering XML tags when a record is modified.

Referring still to FIG. 23, an extension to the simplest embodiment of this inventive feature includes the step of, after XML tags have been removed, re-identifying the XML specification to be used for tag enabling at block 425, re-searching the record as described in the preceding section of this specification to identify information corresponding to specific XMLRSs and reinserting XML tags accordingly (see block 426). This process has the advantage of again rendering an XML ready record which can be used by XML supporting applications.

According to yet another embodiment of this feature, when a segment of a tag enabled record is modified, instead of automatically removing XML tags from the entire record, tags are only removed from an "affected" portion of the record. To this end a first tag set used to earmark a first record segment and other tag sets used to earmark sub-sets of the first record segment are referred to as "related" tag sets. In addition, all tag sets which are related to a high level tag set are also said to be related. Thus, referring again to FIG. 16, the tag set corresponding to XMLRS-7 is related to each of the tag sets corresponding to XMLRS-7-1, XMLRS-7-2, XMLRS-7-3, etc., XMLRS-7-1 is related to XMLRS-7-2 and is related to XMLRS-7-3 and so on. If there were a third level of XMLRSs in FIG. 16 which was dependent from XMLRS-7 (e.g., XMLRS-7-1-1, etc.), tags corresponding thereto would be related to all other XMLRS-7 dependent tag sets.

It has been recognized that only record segments which are related to a modified segment will potentially be affected by the modification. By removing only affected tags the process of researching a record to regenerate tags is reduced appreciably.

Figure 24:
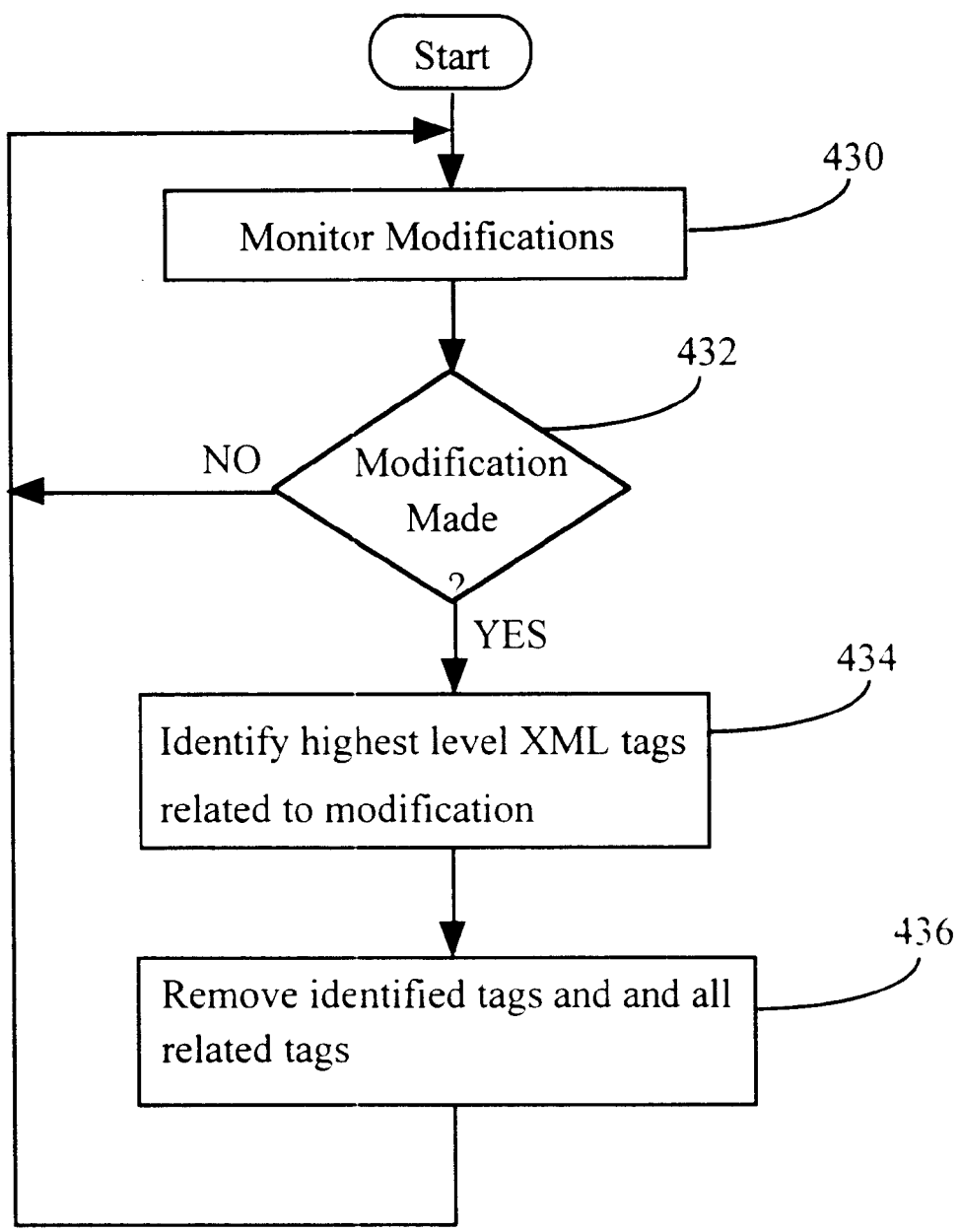
FIG. 24 is similar to FIG. 23, albeit altering the record in a different manner.

An exemplary process 429 whereby only affected tags are removed is illustrated in FIG. 24. At process blocks 430 and 432 record modification are monitored. At block 432, when a modification is identified control passes to block 434. At block 434 processor 14 identifies the highest level XML tags related to the modification. For instance, referring again to FIG. 16, where a modification occurs in a segment earmarked by tags corresponding to XMLRS-7-1 (i.e., in a first claim of a patent specification), processor 14 identifies tags corresponding to XMLRS-7 as the highest level XML tags related to the modification.

Continuing, at block 436 processor 14 removes all tags from the record which are related to the highest level tags which where identified in block 434. Referring again to FIG. 16, if tags corresponding to XMLRS-7 are the highest level tags affected by the modification, all tags associated with XMLRS-7 and XMLRS-7-Q where Q is a digit are removed at block 436. Thereafter control loops back up to process block 430 where additional modifications are monitored.

In another embodiment, when a user attempts to modify (e.g. add text, cut and paste, enter new word, merge text, etc.) a record segment which includes tags, processor 14 may prohibit the modification. In yet another embodiment processor 14 may independently consider each and every XMLRS which corresponds to record tags when a modification is made to the record to determine if the modification renders the XMLRS requirements unmet. Then, when a modified segment no longer meets requirements of one or more XMLRSs, the tags corresponding thereto may be removed.

In yet another embodiment, whenever a tag enabled application accesses a tag enabled record, prior to searching the record for required information, processor 14 automatically strips all tags out of the record, researches the record for segments consistent with the information sought by the application and inserts tags identifying the sought information. In this manner compatibility between the application and record are ensured. In addition, any modifications to the record which may have affected tag correctness are rendered meaningless.

5. Rapid Searching

As records stored on a system proliferate, the number of markup language links and tags which must be supported will grow rapidly such that searching for DRs and MRs and information segments which must be tagged will require a relatively long time. This is particularly true as more intelligence is added to the programs supported by processor 14. For example, each XMLRS DR and MMRs may have 100 or more different rules, most of which will specify, among other things, one or more terms or phrases to be located. Thus, any searching method which speeds up the process of locating a term or phrase within a record or a record segment would greatly enhance the searching, addressing and linking or searching and tagging processes described above.

To this end, the present invention includes a rapid searching method. While useful with searches for single terms, the inventive rapid searching method is particularly useful in searching for phrases or record segments which include more than one term (i.e., segments which include at least one space which separates segment terms).

Figure 28:
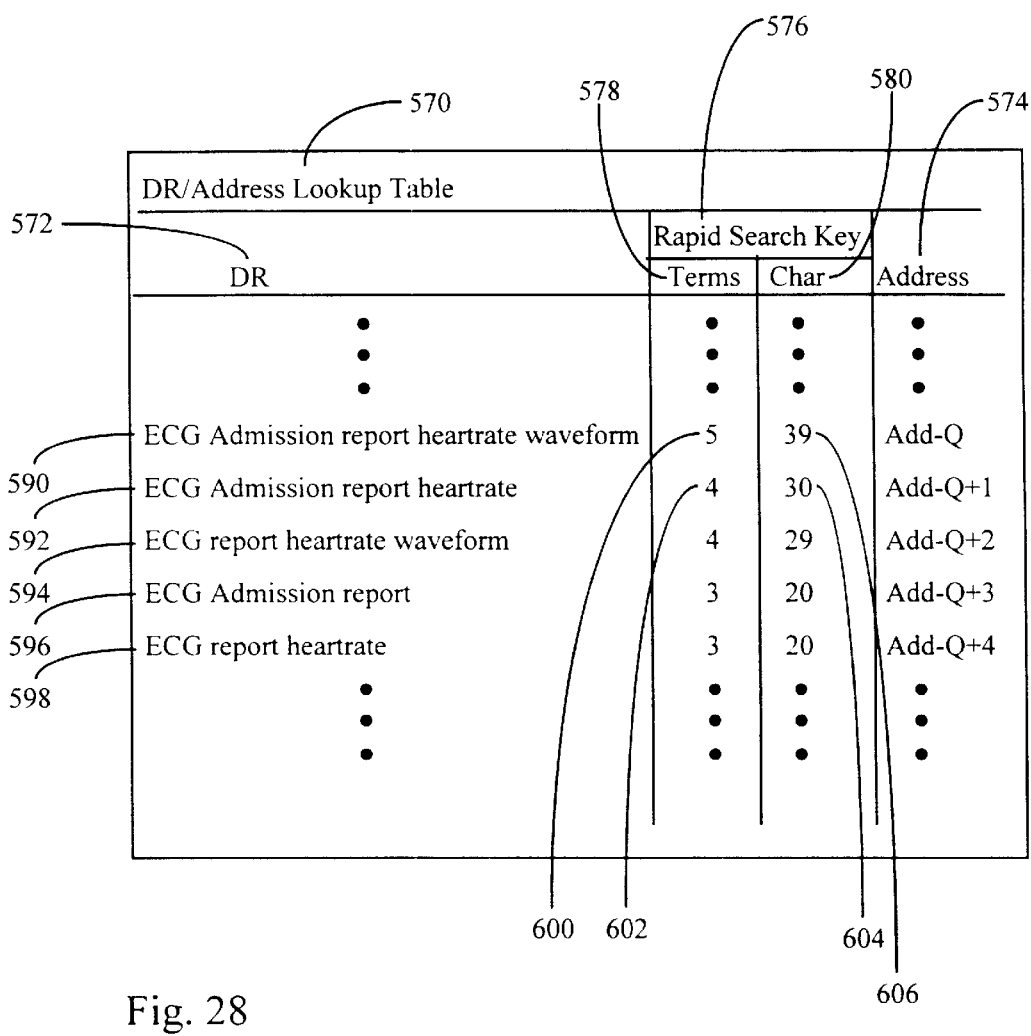
FIG. 28 is a schematic diagram illustrating a DR specification according to the present invention.

To simplify this explanation, although the rapid searching method applies to all searches wherein a term or phrase is sought, the method will be described in the context of a method for searching for DRs. Referring to FIG. 28, an exemplary DR/address lookup table 570 is illustrated which includes a DR column 572 and an address column 574. Column 572 lists all possible DRs to be sought in a record while column 574 lists a separate address for each DR in column 272. DRs in column 572 are listed alphabetically and only a small section of the DR list is illustrated. In one embodiment the alphabetical listing in column 572 is alphabetical with respect to a specific character construct within the DRs. To this end, the character construct may comprise the first characters in the DRs, the characters in a first term in each DR, or any other character construct. Exemplary DRs include "ECG admission report heartrate waveform" 590, "ECG admission report heartrate" 592, "ECG report heartrate waveform" 594, "ECG admission report" 596, "ECG report heartrate" 598, and so on.

In addition to columns 572 and 574, table 570 also includes a rapid search key column 576 which includes data corresponding to at least one and perhaps several DR length characteristics. In the present example only first and second length characteristics are included. Column 576 includes two sub-columns including a "terms" column 578 and a "characters" column 580. Each of columns 578 and 580 includes a list of numbers, a separate number corresponding to each DR in column 572. The number in column 578 indicates the number of terms in the corresponding DR referred to as a DR term count. For example, DR 590 includes five terms and hence the number 5 (i.e., 600) appears in column 578. Similarly, DR 592 includes four terms and hence the number 4 (i.e., 602) appears in column 598.

The number in column 580 indicates the number of characters in the corresponding DR and is referred to as a DR character count. For example, DR 590 includes thirty-nine characters (including spaces) and hence the number 39 (i.e., 604) appears in column 580 while DR 592 includes thirty characters and hence the number 30 (i.e., 606) appears in column 580. Key column 576 is used by processor 14 to rapidly identify DRs.

Figure 29:
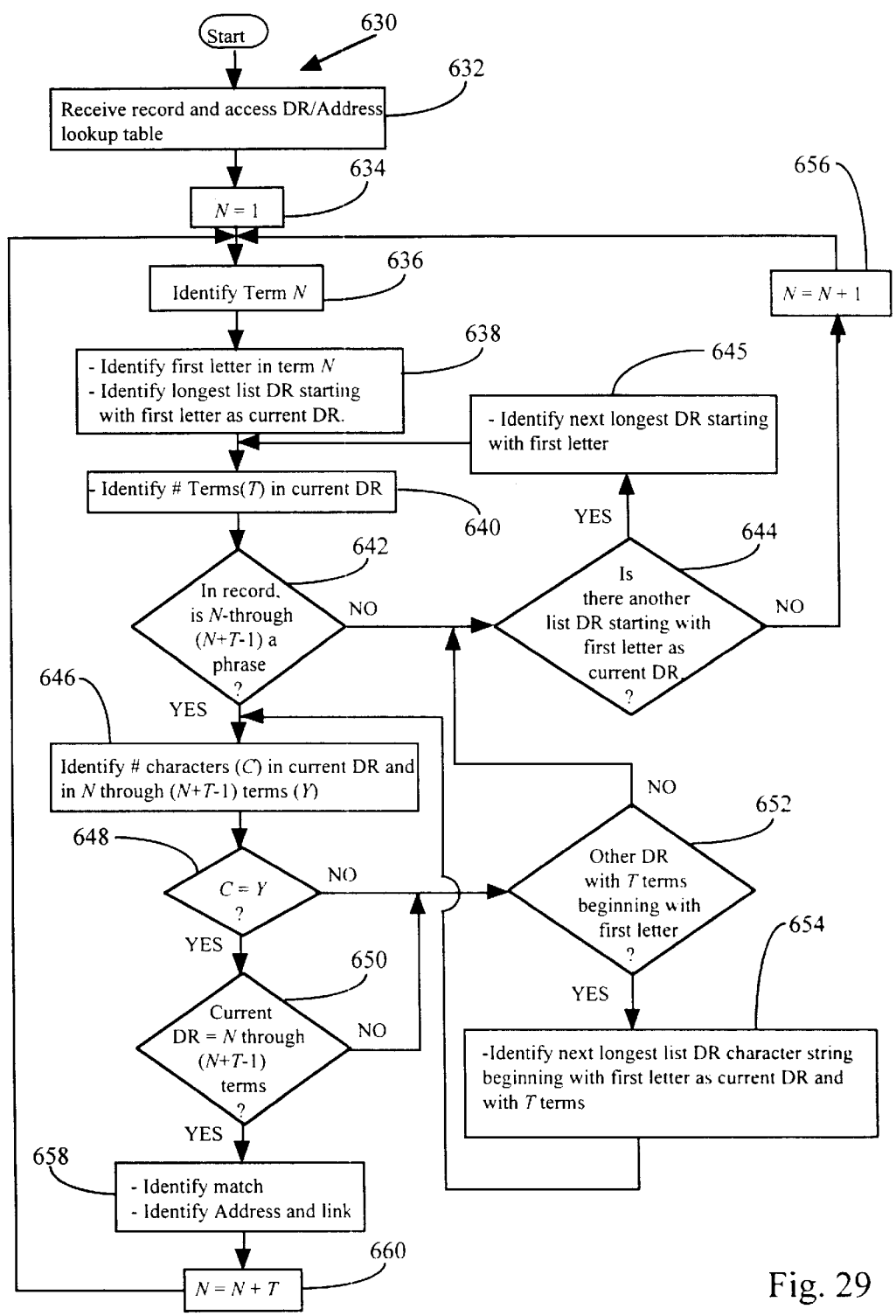
FIG. 29 is a flow chart illustrating an exemplary rapid search method according to the present invention.

An exemplary inventive searching method 630 is illustrated in FIG. 29. Referring to FIGS. 2, 28 and 29, at process block 632, processor 14 receives a record to be searched for DRs and also accesses table 570. At block 634 processor 14 sets a term indicating counter N equal to 1. Counter N indicates which term in a record which is currently considered the first term in a phrase being compared to DRs in list 570, N being incremented during method 630 until all record terms and phrases have been compared to DRs.

At block 636 processor 14 identifies term N. In the present example, because N is currently 1, processor 14 identifies the first term in the record at block 636. At block 638 processor 14 identifies the first character construct in term N. In the present example, it is assumed that the first character construct is the first character or first letter in first term N. At block 636 processor 14 also identifies the longest DR in DR column 572 which begins with the first letter. The longest DR is labeled the "current DR". To facilitate quick identification of the longest DR which begins with a letter, preferably DRs in table 570 are grouped into sub-sets wherein each sub-set includes DRs which begin with the same letter (e.g., "E"). In addition, within each sub-set, preferably, DRs are listed in an order which is related to the number of terms in the DRs. Most preferably longer DRs within a sub-set are listed prior to shorter DRs within the same sub-set.

In the present example it will be assumed that the record being examined begins with the phrase "ECG admission report information is crucial to an understanding . . . ". Thus, term N is "ECG" and the first letter is "E". In addition, at block 638 the longest list DR is "ECG Admission Report heart rate waveform" (see, also 590 in FIG. 28) and is labeled the current DR.

Continuing at block 640 processor 14 identifies the number of terms (T) in current DR 590 as five (i.e., see 600 in FIG. 28) which is referred to as a "first value". Next, at decision block 642 processor 14 determines whether or not terms N through (N+T−1) (i.e., a current segment) corresponds to a complete phrase within the record. For example, assume the record includes the segment " . . . in the ECG report. In addition one has to . . . ". In this case, the four terms which follow term "ECG" are separated by a period and hence form two separate phrases. In this case, control passes to block 644. In the present case, however, in exemplary phrase "ECG admission report information is crucial to an understanding . . . ", terms N (i.e., "ECG") through N+T−1 (i.e., "is") are part of a single phrase and control passes to block 646.

At block 646 processor 14 uses table 570, and specifically column 580, to determine the number of characters (C) (also referred to as a "second value") in the current DR. Column 580 indicates 39 characters and hence second value C=39. In addition, at block 646 processor 14 counts the number of characters (including spaces) which form the phrase which constitutes N through N+T−1 terms. In the exemplary phrase between the first letter of term "ECG" and the last letter of term "is", the N through N+T−1 phrase includes 35 characters and hence Y=35.

At decision block 648 character counts C and Y are compared. Where DR second value C is equal to record character count Y, control passes to decision block 650 which is explained in more detail below. In the alternative, control passes to decision block 652. In the present example, counts C (i.e., 39) and Y (i.e., 35) are not equal and hence control passes to block 652. At block 652 processor 14 determines if there are other DRs in list 570 which include T (i.e., 5) terms which begin with the first letter E. If another DR with 5 terms beginning with letter E exists control passes to block 654 where the other DR with 5 terms beginning with E is selected as the current DR and control passes back to block 640 where the process continues with the new current DR.

In the present case, however, at block 652 there are no other DRs with 5 terms which begin with letter "E" and therefore control passes to block 644. Whenever control passes to block 644 processor 14 determines if there is another DR in table 570 which begins with the first letter and has less than T terms. In the present example, if table 570 does not include another DR beginning with "E" which includes less then T terms, control passes to block 656 where N is incremented by one and then passes back to block 636 where a new first phrase term (i.e., the N+1 term) is selected for DR comparison.

In the present example, referring to FIG. 28, there are several DRs which begin with "E" and have less than five terms and therefore control passes from block 644 to block 645 where the next longest DR starting with letter "E" is selected for DR comparison. Control then passes to block 640. In the present case, the next longest DR beginning with "E" is "ECG admission report heartrate" 592.

Control loops through blocks 640, 642, 646, 648, 652, 654, 644 and 645 several more times until, at block 645, processor 14 identifies DR "ECG Admission Report" 596 (see, FIG. 28). At that point, processes 14 steps through blocks 640 and 642 and control passes to block 646 where DR character count C is identified as 20 and the record phrase character count Y is also identified as 20. Thus, at block 648 counts C and Y are equal and control passes to block 650. At block 650 the current DR and the phrase comprising terms N through N+T−1 are compared. Where the current DR and compared phrase are not identical control again passes to block 652. However, where the DR and compared phrase are identical control passes to block 658 where processor 14 recognizes a DR record phrase match, looks up the corresponding address in table 570 and forms a link. In the present example, DR 596 matches record phrase "ECG Admission Report" and hence address ADD-Q+3 is used to link the DR to the record at address ADD-Q+3.

At block 660 N is incremented by T. in the present example T, the number of terms in the most recent current DR, is 3 and therefore N is incremented to 4 (i.e., 1+3=4). Control then loops back up to block 636 where, in this case, processor 14 identifies the 4th term "information" (i.e., the record began "ECG admission report information is critical to an understanding" and hence the 4th term is "information").

This process of searching and linking continues until all record text has been searched and links formed.

It should be understood that the methods and apparatuses described above are only exemplary and do not limit the scope of the invention, and that various modifications could be made by those skilled in the art that would fall under the scope of the invention. For example, while the invention is generally described in the context of HTML linking and XML tags and rule sets, clearly other linking and tagging systems are contemplated and the invention should not be so limited. In addition, both HTML and XML features described above may be included in a single system to achieve synergistic advantages. In addition, as indicated above, while some preferred resolution rules are described, the invention is not meant to be so limited in its broadest form and generally includes any rule set and processor which applies the set where the rules eliminate ambiguity between DRs and DR/MR combinations.

Moreover, while the exemplary rapid search feature described above includes first and second DR length characteristics (i.e., number of terms and number of characters), other embodiments may include only a single length characteristic or may include many other length characteristics which are examined prior to text comparison. For example, another length characteristic which may be used might be the number of characters in a first term in a record phrase which is compared to the number of characters in the first term of a DR. The important aspect of the rapid search feature is that DRs include characteristics in addition to their characters which can be sought to narrow the possible DRs to a small number prior to character comparison and that searching for such additional characteristics is much more rapid than a full fledged character search. In other words, each search time is decreased appreciably by performing a rapid DR search based on DR length characteristics to narrow the possible DR list and then performing a detailed character search to identify a specific DR from the narrow list of possible DRs.

Furthermore, the rapid search method may be employed on a single phrase (as opposed to an entire record) or may include a DR list which is not alphabetized or using a single DR as opposed to a DR list or, may require a processor to identify DR length characteristics prior to comparison instead of relying on a table key.

Moreover, after an SR is associated with a record or record segment, the inventive system may also monitor modifications to the record and, when a modification would alter the correctness of the SR-record association the system may be programmed to change the association through eliminating the association, re-identifying if another suitable SR-record association exists and creating any suitable SR-record association.

To apprise the public of the scope of this invention, the following claims are made:

What is claimed is:

1. A method for identifying a referenced record referenced in a referencing record wherein the referenced record is referenced in the referencing record by at least a combination including a data reference (DR) and a modifier reference (MR), the method comprising the steps of:
   (i) receiving the referencing record;
   (ii) analyzing the referencing record to identify a DR, when a DR is identified:
      (a) identifying an MR rule set (MRRS) specifying the relationship between an MR and the DR;
      (b) analyzing the referencing record in accordance with the MRRS to identify the existence of the MR and, when the MR is identified;
      (c) identifying the referenced record associated with the DR/MR combination.

2. The method of claim 1 wherein a specifying reference SR includes one of a DR/MR pair and a DR, at least one short SR consists of a portion of a long SR and, when a record segment which constitutes the short SR also constitutes a portion of the long SR, the step of identifying the DR includes identifying the DR corresponding to the long SR and, where the long SR includes an MR, the step of identifying the MR includes identifying the MR corresponding to the long SR.

3. The method of claim 1 for use with a database (DB) including at least one address format specifying an address format of the referenced record address, the method further including the step of using the address format to form an address for the DR/MR combination.

4. The method of claim 3 further including the step of using information from the referencing record to form the address of the referenced record as specified by the address format.

5. The method of claim 1 wherein the step of analyzing includes searching the referencing record using natural language processing.

6. The method of claim 1 wherein the MRRS specifies a search range of data about the DR which is to be searched for an MR and the step of analyzing in accordance with the MRRS includes searching the range to identify the MR.

7. The method of claim 6 wherein at least the referencing record is a text document and the search range is a range of terms which precede and follow the DR.

8. The method of claim 7 wherein the range is selected from a list including a text fragment, a sentence segment in which the DR appears, the sentence in which the DR appears, the paragraph in which the DR appears, a document and a table cell.

9. The method of claim 6 wherein there are at least first and second referenced records referenced in the referencing record which correspond to first and second DR/MR combinations and first and second MRRSs, respectively, and, wherein, when either of the DR or MR in the first combination is within the second MRRS search range, the second MRRS search range is modified.

10. The method of claim 9 wherein the search range is modified by restricting the second search range such that the modified range is limited by the DR or MR from the first combination which is within the second MRRS search range.

11. The method of claim 6 wherein there are at least first and second DRs which may form first and second DR/MR combinations with a single MR, the MRRS includes at least first and second MRRSs corresponding to the first and second DR/MR combinations, respectively and the step of analyzing to identify an MR includes the steps of:

when one of the first or second DR/MR combinations is identified, determining if the MR is within a search range of the DR in the other of the DR/MR combinations; and if the MR is within the search range of the DR in the other of the combinations, selecting one of the DR/MR combinations for identifying the referenced record.

12. The method of claim 11 wherein the step of selecting includes determining which of the first and second DRs is closest to the MR and selecting the corresponding DR/MR combination.

13. The method of claim 11 wherein the step of analyzing includes searching the referencing record using natural language processing.

14. The method of claim 1 wherein DRs may overlap and, when first and second DRs overlap, the method includes the step of identifying one of the first and second overlapping DRs.

15. The method of claim 14 wherein the step of identifying one of the first and second includes identifying the longest DR.

16. The method of claim 14 wherein the step of identifying one of the first and second includes identifying the first.

17. The method of claim 1 including at least first and second DR/MR combinations including the same DR, the first and second DR/MR combinations corresponding to first and second MRRSs, the MRRSs specifying search ranges of MRs with respect to DRs, the step of analyzing to identify an MR including the steps of:

when one of the first or second DR/MR combinations is identified, determining if the MR in the other of the DR/MR combinations is within the search range of the DR specified by the corresponding MRRS; and if the MR in the other of the combinations is within the search range of the DR, selecting one of the DR/MR combinations for identifying the referenced record.

18. The method of claim 17 wherein the MRRSs include resolution rules for resolving which of two DR/MR combinations to select and the step of selecting includes applying the resolution rules.

19. The method of claim 1 wherein MRs include text and at least one long MR includes a short MR and additional text and wherein, when the long MR appears in the text, the step of identifying the MR includes identifying the long MR.

20. The method of claim 1 wherein DRs include text and at least one long DR includes a short DR and additional text and wherein, when the long DR appears in the text, the step of identifying the DR includes identifying the long DR.

21. The method of claim 20 wherein MRs include text and at least one long MR includes a short MR and additional text and wherein, when the long MR appears in the text, the step of identifying the MR includes identifying the long MR.

22. The method of claim 1 wherein there are at least first and second MR levels, the first level including MR1s which modify the DR and the second level including MR2s which modify MR1s, the MRRSs including rules specifying relationships between DRs and MR1s and between MR1s and MR2s, some records referenceable by a combination of a DR and an MR1 and other records referenceable by a combination of a DR, an MR1 and an MR2 wherein the step of analyzing to identify an MR includes:

analyzing to identify an MR1 and where an MR1 is identified:
analyzing to identify an MR2 and, when an MR2 is identified, identifying the record associated with the DR/MR1/MR2 combination;
else identifying the record associated with the DR/MR1 combination.

23. The method of claim 1 wherein the step of receiving includes receiving the record as the record is created and the step of analyzing includes analyzing the record as the record is created.

24. The method of claim 1 further including the step of linking the record reference to the referenced record.

25. The method of claim 24 wherein the step of linking includes automatic retrieval of the linked record.

26. The method of claim 24 wherein the step of linking including modifying the appearance of the DR/MR combination and linking the DR/MR combination to the address of the referenced record such that, when the DR/MR combination is selected, the referenced record is provided.

27. A method to be used with a rule set including subject matter specific tag pairs and corresponding search rules, a separate tag pair for each of a plurality of different information types and a separate search rule for each pair, each pair including a begin tag and an end tag, the method comprising the steps of:

(a) receiving a record;
(b) examining the record according to the search rules to identify record segments including information of each of the information types;
(c) when a record segment is identified which is of a particular information type:
accessing the tag pair associated with the information type; inserting the begin tag before the identified segment and inserting the end tag after the identified segment.

28. The method of claim 27 further including the step of performing a function on the record after tag insertion.

29. The method of claim 28 wherein the step of performing a function includes the step of storing the record for subsequent use.

30. The method of claim 28 wherein the step of performing a function includes retrieving at least one record segment by identifying a specific tag pair.

31. The method of claim 27 wherein the rule set is a first rule set and the method is to be used with a plurality of rule sets and wherein the method further includes the steps of, prior to examining, determining which rule set to use for the exam.

32. The method of claim 31 wherein the record includes information which can be used to determine which of the plurality of rule sets to use for the exam and wherein the step of determining which rule set to use includes examining the record information.

33. The method of claim 27 wherein the step of receiving includes receiving the record as the record is created and the step of analyzing includes analyzing the record as the record is created.

34. The method of claim 27 wherein the tags are mark-up language tags.

35. The method of claim 27 further including the step of, after receiving the record and prior to examining the record, determining if any tag pairs exist in the record and, if tag pairs exist in the record, stripping the tag pairs from the record.

36. The method of claim 27 wherein the step of receiving includes receiving the record as the record is created and wherein, after a tag pair has been inserted, if the segment corresponding to the tag pair is altered, the tag pair corresponding thereto is modified.

37. The method of claim 36 wherein the step of modifying includes deleting the tag pair.

38. The method of claim 37 wherein the step of modifying, after deleting, further includes repeating steps (a) through (d) to determine if another tag pair should be inserted in the record and, if so, to insert the tag pair in the record.

39. A method to be used with a rule set including subject matter specific tag pairs and corresponding search rules, a separate tag pair for each of a plurality of different information types and a separate search rule for each pair, each pair including a begin tag and an end tag, the method comprising the steps of:

(a) receiving a record;

(b) examining the record according to the search rules to identify record segments including information of each of the information types;

(c) when a record segment is identified which is of a particular information type:

accessing the tag pair associated with the information type; inserting the begin tag before the identified segment and inserting the end tag after the identified segment wherein information of a first type corresponds to a first level pair, a segment corresponding to the first type is a first segment and the rule set includes at least one second level pair and a second level search rule, the second level pair and rule corresponding to a second level sub-set of the first type subject matter, the method further including the steps of, after identifying a first segment and prior to the step of performing:

examining the first segment according to the second level search rule to identify a second segment corresponding to the second level sub-set;

when a second segment is identified, inserting the second level begin tag before the second segment and after the first level begin tag; and inserting the second level end tag after the second segment and before the first level end tag.

40. The method of claim 39 wherein the rule set includes at least one third level pair and a third level search rule, the third level pair and rule corresponding to a third level sub-set which is s sub-set of the second level sub-set, the method further including the steps of, after identifying a second segment and prior to the step of performing:

examining the second segment according to the third level search rule to identify a third segment corresponding to the third level sub-set;

when a third segment is identified, inserting the third level begin tag before the third segment and after the second level begin tag; and inserting the third level end tag after the third segment; inserting the second level end tag after the second segment and before the second level end tag.

41. A method to be used with a processor capable of allowing access to at least a first record, displaying at least the first record on a screen for viewing, facilitating at least a sub-set of possible record modifications including copying, moving, altering and deleting, at least a first record segment having a first characteristic set which distinguishes the segment from other record segments, the first record including information tags which can be used by the processor and other processors to distinguish the first segment from other record segments, the method for limiting record modifications when any of the possible record modifications are performed on the first record, the method comprising the steps of:

monitoring modifications to the record;

identifying record modifications which modify the characteristics of the first record segment;

when a first record segment characteristic is modified, limiting first record segment modification.

42. The method of claim 41 wherein the step of limiting includes prohibiting the modification.

43. The method of claim 41 wherein the step of limiting includes determining if the modification distinguishes the segment from the first characteristic set and, if the modification distinguishes the segment, eliminating the information tags.

44. The method of claim 43 wherein there are additional characteristic sets which correspond to additional information tags and, wherein the step of limiting further includes the steps of, if the information tags corresponding to the first characteristic set are eliminated, after eliminating the tags, determining if the characteristics of any segment of the document match one of the characteristic sets and, if a segment matches one of the characteristic sets, inserting information tags corresponding to the matching characteristic set into the record to distinguish the matching segment from other record segments.

45. The method of claim 41 wherein the processor is a word processor and the records includes at least some text and wherein the step of monitoring includes monitoring modifications to text segments.

46. The method of claim 41 wherein the information tags are XML tags.

47. A method for identifying a referenced record referenced in a referencing record wherein the referenced record is referenced in the referencing record by at least a data reference (DR), the method comprising the steps of:

as the referencing record is created:

(i) receiving the referencing record;

(ii) analyzing the referencing record to identify a DR; and (iii) when a DR is identified, associating the DR and the referenced record.

48. The method of claim 47 wherein the step of associating includes determining the address of the referenced record and forming a link between the DR and the referenced record.

49. The method of claim 48 for use with a database including a table of DRs and associated record addresses and wherein the step of determining the address includes the steps of locating a DR in the table and correlating an address with the DR.

50. The method of claim 47 wherein the step of associating includes linking the DR to the referenced record.

51. The method of claim 50 wherein the step of associating includes modifying the appearance of the DR and linking the DR to the address of the referenced record such that when the DR is selected, the referenced record is accessed.

52. The method of claim 47 wherein DRs include text and at least one long DR includes a short DR and additional text and wherein, when the long DR appears in the text, the step of analyzing to identify the DR includes identifying the long DR.

53. The method of claim 47 wherein a modifier reference (MR) can be used in conjunction with a DR to reference a record and at least one record is referenced by a DR/MR combination and the method further includes the steps of:

after identifying the DR and prior to associating the DR, examining the record for an MR and, when an MR is identified, associating the DR/MR combination with the referenced record.

54. The method of claim 47 further including the steps of, after the step of associating, monitoring changes to the record and when an associated DR is modified, changing the association.

55. The method of claim 54 wherein the step of changing the association includes eliminating the association.

56. A method for identifying referenced records referenced in a referencing record wherein the referenced records are each referenced in the referencing record by data references (DRs) and where at least a first DR includes a portion of a second DR, the method comprising the steps of:
 (i) receiving the referencing record;
 (ii) analyzing the referencing record to identify DRs, when two overlapping DRs are identified:
  (a) selecting one of the DRs; and
  (b) identifying the referenced record associated with the selected DR.

57. The method of claim 56 wherein the step of selecting includes selecting the first DR.

58. The method of claim 56 wherein a resolution rule set (RRS) exists for determining which of two overlapping DRs to select and the step of selecting includes applying the RRS to the overlapping DRs.

59. The method of claim 56 wherein at least one long DR includes a short DR and additional text and wherein the step of selecting includes selecting the longest DR.

60. The method of claim 56 wherein the step of analyzing includes using natural language processing to identify DRs.

61. A method for searching for a plurality of data references in a record which includes terms which form record phrases, each data reference characterized by a number of terms and a number of characters, the data references arranged in a table, each data reference in the table beginning with a first character construct, the data references organized such that their first character constructs are alphabetically ordered, each set of data references which begin with the same character construct forming a data reference sub-set, the method comprising the steps of:
a) identifying a first term in the record as a current term;
b) identifying a first character construct in the current term;
c) identifying a data reference sub-set which begins with the current term first character construct;
d) identifying a data reference from the sub-set as a current data reference;
e) identifying the number of terms T in the current data reference;
f) identifying the current term and the following (T-1) terms in the record as a current segment;
g) determining if the current segment forms a single phrase;
 I) if the current segment forms a single phrase:
  1) identifying the number of characters in the current data reference;
  2) determining if the current segment includes the same number of characters as the current data reference;
   a) if the current segment includes the same number of characters as the current data reference:
    i) comparing the text of the current segment to the current data reference text to determine if the texts are identical:
    if the texts are identical, performing a function and then determining if there is at least one record term which follows the last current segment term and, if there is at least one record term which follows the last current segment term, selecting the term which follows the current segment as the current term and repeating steps (b) through (g);
    else, skip to step (g)(II)(1);
 II) else:
  1) determining if all of the sub-set data references have been compared to a segment beginning with the current term, and, if all of the sub-set data references have been compared to a segment beginning with the current term, skipping to step (h), else, selecting another sub-set data reference as the current data reference and repeating steps (e) through (g);
h) selecting the term following the current term as a new current term and repeating steps (b) through (g).

62. The method of claim 61 wherein the first character construct is the first character of the first term.

63. The method of claim 61 wherein the first character construct includes the characters of the first term.

64. A method for searching for at least one data reference in a record which includes terms which form record phrases wherein the data reference is characterized by at least a first quantifiable data reference length characteristic, the method comprising the steps of:
 a) identifying a data reference as a current data reference;
 b) identifying a first value which is the value of the current data reference first length characteristic;
 c) identifying a record phrase to be searched; and
 d) comparing the record phrase first length characteristic and the first value; and
  1) if the record phrase first length characteristic and first value are identical, comparing phrase text to current data reference text to determine if the phrase text and current data reference text are identical and, if identical, performing a function;
  2) else, concluding that the record phrase and the current data reference are different.

65. The method of claim 64 wherein the data reference is a first data reference and there are a plurality of additional data references, each additional reference having a reference specific first length characteristic value and, wherein, the method further includes the steps of:
 (e) when it is concluded that the current data reference and the phrase are different, repeating steps (b) through (d) with another of the data references as the current data reference; and
 (f) repeating step (e) for each of at least a sub-set of the additional data references.

66. The method of claim 65 wherein the first length characteristic is a data reference term count.

67. The method of claim 66 wherein the data references and term counts are correlated in a lookup table and wherein the step of identifying a current value includes the step of identifying the term count in the table.

68. The method of claim 67 wherein each data reference in the table begins with a data reference specific first character construct, the data references are organized such that their constructs are alphabetically ordered, each set of data references which begin with the same character construct forms a data reference sub-set and the method further includes the steps of, prior to identifying a data reference, identifying a term in a record which will form the first term in the record phrase, identifying the first character construct in the identified term, identifying the data reference sub-set which includes data references which begin with the first character construct in the term and limiting the search to the identified data reference sub-set.

69. The method of claim 68 wherein the first character construct is the first character of the identified term.

70. The method of claim 68 wherein the first character construct includes the characters in the identified term.

71. The method of claim 68 wherein data references within a sub-set are searched in an order which is a function of the relative data reference term counts.

72. The method of claim 71 wherein data references with relatively larger term counts are searched prior to data references with relatively shorter term counts.

73. The method of claim 72 wherein each data reference is also characterized by a second length characteristic and the table also correlates each data reference with a second value which is a second length characteristic value and, wherein, the method further includes the steps of, after determining that the record phrase first length characteristic and the first value are identical and prior to comparing the phrase and data reference texts, identifying the second value corresponding to the current data reference, comparing the record phrase second length characteristic and the second value, if the second record phrase characteristic and the second value are identical, comparing the text, else concluding that the record phrase and the current data reference are different.

74. The method of claim 73 wherein the second value indicates the data reference character count.

75. The method of claim 74 wherein the method is for searching for all data references within a record and wherein the method is repeated for at least a sub-set of all record phrases within a record.

76. The method of claim 75 wherein record phrases are searched consecutively beginning with the first record phrase and ending with the last record phrase and, wherein, when a data reference and a specific record phrase are identical, the next phrase to be searched begins with the term immediately following the specific record phrase.

77. The method of claim 76 wherein the record includes a plurality of terms, the step of identifying a record phrase including the steps of, after identifying the number of terms in a data reference, selecting a record segment as a segment beginning with a record term and including the number of terms in the data reference, the step of comparing the record phrase first length characteristic and the data reference first length characteristic value including the steps of determining the number of terms in a record phrase by determining if the terms in the record segment constitute a single phrase, where the terms in the record segment constitute a single phrase, determining that the record phrase first length characteristic is identical to the data reference first length characteristic, else concluding that the record phrase and the current data reference are different.

78. The method of claim 64 wherein the first length characteristic is a data reference term count.

79. The method of claim 78 wherein the data reference is also characterized by a second length characteristic and, wherein, the method further includes the steps of identifying a second data reference length characteristic value which is a second value and, after determining that the record phrase first length characteristic and the first value are identical and prior to comparing the phrase and data reference texts, comparing the record phrase second length characteristic and the second value, if the second record phrase charac-teristic and the second value are identical, comparing the text, else concluding that the record phrase and the data reference are different.

80. The method of claim 79 wherein the second length characteristic is a data reference character count.

81. The method of claim 80 for use with a look-up table which correlates the data reference and the first and second values and wherein the steps of identifying the data reference first and second values include the steps of identifying the values in the look-up table, respectively.

82. The method of claim 64 wherein the first length characteristic is a data reference character count.

83. A method for use with a system capable of recognizing specifying references (SRs) in a record which reference another record and forming links between the SRs and the referenced records, the method for eliminating ambiguity when SRs overlap and comprising the steps of:

(i) receiving a referencing record;
(ii) analyzing the referencing record to identify SRs;
(iii) when two or more SRs overlap, enabling an operator to select at least one of the SRs;
(iv) identifying the referenced records associated with the selected SRs; and
(v) linking the selected SRs to corresponding records.

84. The method of claim 83 wherein the step of enabling includes providing an SR list indicating possible SRs and providing a tool for selecting a sub-set of the SRs.

85. The method of claim 84 wherein the step of linking includes presenting the selected SRs in a selectable format and linking the SRs to corresponding records such that when an SR is selected, the corresponding record is provided.

86. A method for use with an application wherein specifying references (SRs) in one record to other records which are selectable to access the other records are visually distinguished from other record information so as to indicate selectability, the method also for use with a system which enables a user to designate and also select SRs where designation comprises pointing to an SR without selection and, wherein a seemingly general SR is modified by other record information which renders the SR relatively specific, the method for indicating the specific nature of an SR prior to selection and comprising the steps of:

when an SR is designated, indicating the specific nature of the SR.

87. The method of claim 86 wherein the step of indicating includes opening a description window and indicating the specific nature within the window.

88. The method of claim 86 wherein SRs may overlap and, wherein, when SRs overlap and any portion of an overlapping SR is designated, the method further includes the step of indicating each of the overlapping SRs and enabling a user to select any one of the overlapping SRs for linking purposes.

89. A method for use with an application wherein specifying references (SRs) in one record to other records which are selectable to access the other records are visually distinguished from other record information so as to indicate selectability, the method also for use with a system which enables a user to designate and also select SRs where designation comprises pointing to an SR without selection and, wherein some SRs may overlap, the method for eliminating ambiguity when SRs overlap and comprising the steps of:

when SRs overlap and any portion of an overlapping SR is designated, indicating each of the overlapping SRs and enabling a user to select any one of the overlapping SRs for linking purposes.

90. The method of claim 89 wherein the step of indicating includes opening a description window and indicating each of the overlapping SRs.

91. An apparatus for identifying a referenced record referenced in a referencing record wherein the referenced record is referenced in the referencing record by at least a combination including a data reference (DR) and a modifier reference (MR), the apparatus comprising:

a processor running a pulse sequencing program to perform the steps of:
(i) receiving the referencing record;
(ii) analyzing the referencing record to identify a DR, when a DR is identified:
(a) identifying an MR rule set (MRRS) specifying the relationship between an MR and the DR;
(b) analyzing the referencing record in accordance with the MRRS to identify the existence of the MR and, when the MR is identified;
(c) identifying the referenced record associated with the DR/MR combination.

92. The apparatus of claim 91 wherein a specifying reference SR includes one of a DR/MR pair and a DR, at least one short SR consists of a portion of a long SR and, when a record segment which constitutes the short SR also constitutes a portion of the long SR, the processor identifies the DR by identifying the DR corresponding to the long SR and, where the long SR includes an MR, the processor identifies the MR by identifying the MR corresponding to the long SR.

93. The apparatus of claim 91 for use with a database (DB) including at least one address format specifying an address format of the referenced record address, the processor further using the address format to form an address for the DR/MR combination.

94. The apparatus of claim 93 wherein the processor further uses information from the referencing record to form the address of the referenced record as specified by the address format.

95. The apparatus of claim 91 wherein the processor analyzes by searching the referencing record using natural language processing.

96. The apparatus of claim 91 wherein the MRRS specifies a search range of data about the DR which is to be searched for an MR and the processor analyzes in accordance with the MRRS by searching the range to identify the MR.

97. The apparatus of claim 96 wherein at least the referencing record is a text document and the search range is a range of terms which precede and follow the DR.

98. The apparatus of claim 97 wherein the range is selected from a list including a text fragment, a sentence segment in which the DR appears, the sentence in which the DR appears, the paragraph in which the DR appears, a document and a table cell.

99. The apparatus of claim 96 wherein there are at least first and second referenced records referenced in the referencing record which correspond to first and second DR/MR combinations and first and second MRRSs, respectively, and, wherein, when either of the DR or MR in the first combination is within the second MRRS search range, the processor modifies the second MRRS search range.

100. The apparatus of claim 99 wherein the processor modifies the search range by restricting the second search range such that the modified range is limited by the DR or MR from the first combination which is within the second MRRS search range.

101. The apparatus of claim 96 wherein there are at least first and second DRs which may form first and second DR/MR combinations with a single MR, the MRRS includes at least first and second MRRSs corresponding to the first and second DR/MR combinations, respectively and the processor analyzes to identify an MR by:

when one of the first or second DR/MR combinations is identified, determining if the MR is within a search range of the DR in the other of the DR/MR combinations; and if the MR is within the search range of the DR in the other of the combinations, selecting one of the DR/MR combinations for identifying the referenced record.

102. The apparatus of claim 101 wherein the processor selects by determining which of the first and second DRs is closest to the MR and selecting the corresponding DR/MR combination.

103. The apparatus of claim 101 wherein the processor analyzes by searching the referencing record using natural language processing.

104. The apparatus of claim 91 wherein DRs may overlap and, when first and second DRs overlap, the processor identifies one of the first and second overlapping DRs.

105. The apparatus of claim 104 wherein the processor identifies one of the first and second by identifying the longest DR.

106. The apparatus of claim 104 wherein the processor identifies one of the first and second by identifying the first.

107. The apparatus of claim 91 including at least first and second DR/MR combinations including the same DR, the first and second DR/MR combinations corresponding to first and second MRRSs, the MRRSs specifying search ranges of MRs with respect to DRs, the processor analyzes to identify an MR by:

when one of the first or second DR/MR combinations is identified, determining if the MR in the other of the DR/MR combinations is within the search range of the DR specified by the corresponding MRRS; and if the MR in the other of the combinations is within the search range of the DR, selecting one of the DR/MR combinations for identifying the referenced record.

108. The apparatus of claim 107 wherein the MRRSs include resolution rules for resolving which of two DR/MR combinations to select and the processor selects by applying the resolution rules.

109. The apparatus of claim 91 wherein MRs include text and at least one long MR includes a short MR and additional text and wherein, when the long MR appears in the text, the processor identifies the MR by identifying the long MR.

110. The apparatus of claim 91 wherein DRs include text and at least one long DR includes a short DR and additional text and wherein, when the long DR appears in the text, the processor identifies the DR by identifying the long DR.

111. The apparatus of claim 110 wherein MRs include text and at least one long MR includes a short MR and additional text and wherein, when the long MR appears in the text, the processor identifies the MR by identifying the long MR.

112. The apparatus of claim 91 wherein there are at least first and second MR levels, the first level including MR1s which modify the DR and the second level including MR2s which modify MR1s, the MRRSs including rules specifying relationships between DRs and MR1s and between MR1s and MR2s, some records referenceable by a combination of a DR and an MR1 and other records referenceable by a combination of a DR, an MR1 and an MR2 wherein the processor analyzes to identify an MR by:

analyzing to identify an MR1 and where an MR1 is identified:

analyzing to identify an MR2 and, when an MR2 is identified, identifying the record associated with the DR/MR1/MR2 combination.

else identifying the record associated with the DR/MR1 combination.

113. The apparatus of claim 91 wherein the processor receives by receiving the record as the record is created and the processor analyzes by analyzing the record as the record is created.

114. The apparatus of claim 113 wherein the rule set includes at least one third level pair and a third level search rule, the third level pair and rule corresponding to a third level sub-set which is s sub-set of the second level sub-set, the apparatus further performing the steps of, after identifying a second segment and prior to the step of performing:

examining the second segment according to the third level search rule to identify a third segment corresponding to the third level sub-set;

when a third segment is identified, inserting the third level begin tag before the third segment and after the second level begin tag; and inserting the third level end tag after the third segment; inserting the second level end tag after the second segment and before the second level end tag.

115. The apparatus of claim 91 wherein the processor further links the record reference to the referenced record.

116. The apparatus of claim 115 wherein the processor links by automatic retrieval of the linked record.

117. The apparatus of claim 115 wherein the processor links by modifying the appearance of the DR/MR combination and linking the DR/MR combination to the address of the referenced record such that, when the DR/MR combination is selected, the referenced record is provided.

118. An apparatus to be used with a rule set including subject matter specific tag pairs and corresponding search rules, a separate tag pair for each of a plurality of different information types and a separate search rule for each pair, each pair including a begin tag and an end tag, the apparatus:

a processor running a pulse sequencing program to perform the steps of:
(a) receiving a record;
(b) examining the record according to the search rules to identify record segments including information of each of the information types;
(c) when a record segment is identified which is of a particular information type:
accessing the tag pair associated with the information type; inserting the begin tag before the identified segment and inserting the end tag after the identified segment.

119. The apparatus of claim 118 wherein the processor further performs the step of performing a function on the record after tag insertion.

120. The apparatus of claim 119 wherein the processor performs a function by storing the record for subsequent use.

121. The apparatus of claim 119 wherein the processor performs a function by retrieving at least one record segment by identifying a specific tag pair.

122. The apparatus of claim 118 wherein the rule set is a first rule set and the apparatus is to be used with a plurality of rule sets and wherein the processor further, prior to examining, determines which rule set to use for the exam.

123. The apparatus of claim 122 wherein the record includes information which can be used to determine which of the plurality of rule sets to use for the exam and wherein the processor determines which rule set to use by examining the record information.

124. The apparatus of claim 118 wherein the processor receives by receiving the record as the record is created and the processor analyzes by analyzing the record as the record is created.

125. The apparatus of claim 118 wherein information of a first type corresponds to a first level pair, a segment corresponding to the first type is a first segment and the rule set includes at least one second level pair and a second level search rule, the second level pair and rule corresponding to a second level sub-set of the first type subject matter, the apparatus further performing the steps of, after identifying a first segment and prior to the step of performing:

examining the first segment according to the second level search rule to identify a second segment corresponding to the second level sub-set;

when a second segment is identified, inserting the second level begin tag before the second segment and after the first level begin tag; and inserting the second level end tag after the second segment and before the first level end tag.

126. The apparatus of claim 117 wherein the tags are mark-up language tags.

127. The apparatus of claim 117 wherein the processor further performs the steps of, after receiving the record and prior to examining the record, determining if any tag pairs exist in the record and, if tag pairs exist in the record, stripping the tag pairs from the record.

128. The apparatus of claim 117 wherein the processor receives by receiving the record as the record is created and wherein, after a tag pair has been inserted, if the segment corresponding to the tag pair is altered, the processor modifies the corresponding tag pair.

129. The apparatus of claim 128 wherein the processor modifies by deleting the tag pair.

130. The apparatus of claim 129 wherein the processor modifies by, after deleting, further repeating steps (a) through (d) to determine if another tag pair should be inserted in the record and, if so, to insert the tag pair in the record.

131. An apparatus to be used with a processor capable of allowing access to at least a first record, displaying at least the first record on a screen for viewing, facilitating at least a sub-set of possible record modifications including copying, moving, altering and deleting, at least a first record segment having a first characteristic set which distinguishes the segment from other record segments, the first record including information tags which can be used by the processor and other processors to distinguish the first segment from other record segments, the apparatus for limiting record modifications when any of the possible record modifications are performed on the first record, the apparatus comprising:

a processor running a pulse sequencing program to perform the steps of:
monitoring modifications to the record;
identifying record modifications which modify the characteristics of the first record segment;
when a first record segment characteristic is modified, limiting first record segment modification.

132. The apparatus of claim 131 wherein the processor limits by prohibiting the modification.

133. The apparatus of claim 131 wherein the processor limits by determining if the modification distinguishes the segment from the first characteristic set and, if the modification distinguishes the segment, eliminating the information tags.

134. The apparatus of claim 133 wherein there are additional characteristic sets which correspond to additional information tags and, wherein the processor limits further by, if the information tags corresponding to the first characteristic set are eliminated, after eliminating the tags, determining if the characteristics of any segment of the document match one of the characteristic sets and, if a segment matches one of the characteristic sets, inserting information tags corresponding to the matching characteristic set into the record to distinguish the matching segment from other record segments.

135. The apparatus of claim 131 wherein the processor is a word processor and the records includes at least some text and wherein the processor monitor by monitoring modifications to text segments.

136. The apparatus of claim 131 wherein the information tags are XML tags.

137. An apparatus for identifying a referenced record referenced in a referencing record wherein the referenced record is referenced in the referencing record by at least a data reference (DR), the apparatus comprising:
  a processor running a pulse sequencing program to perform the steps of, as a referencing record is created:
    (i) receiving the referencing record;
    (ii) analyzing the referencing record to identify a DR; and
    (iii) when a DR is identified, associating the DR and the referenced record.

138. The apparatus of claim 137 wherein the processor associates by determining the address of the referenced record and forming a link between the DR and the referenced record.

139. The apparatus of claim 138 for use with a database including a table of DRs and associated record addresses and wherein the processor determines the address by locating a DR in the table and correlating an address with the DR.

140. The apparatus of claim 137 wherein the processor associates by linking the DR to the referenced record.

141. The apparatus of claim 140 wherein the processor associates by modifying the appearance of the DR and linking the DR to the address of the referenced record such that when the DR is selected, the referenced record is accessed.

142. The apparatus of claim 137 wherein DRs include text and at least one long DR includes a short DR and additional text and wherein, when the long DR appears in the text, the processor analyzes to identify the DR by identifying the long DR.

143. The apparatus of claim 137 wherein a modifier reference (MR) can be used in conjunction with a DR to reference a record and at least one record is referenced by a DR/MR combination and the processor further performs the steps of:
  after identifying the DR and prior to associating the DR, examining the record for an MR and, when an MR is identified, associating the DR/MR combination with the referenced record.

144. The apparatus of claim 137 wherein the processor further performs the steps of, after the step of associating, monitoring changes to the record and when an associated DR is modified, changing the association.

145. The apparatus of claim 144 wherein the processor changes the association by eliminating the association.

146. A apparatus for identifying referenced records referenced in a referencing record wherein the referenced records are each referenced in the referencing record by data references (DRs) and where at least a first DR includes a portion of a second DR, the apparatus comprising:
  a processor running a pulse sequencing program to perform the steps of:
    (i) receiving the referencing record;
    (ii) analyzing the referencing record to identify DRs, when two overlapping DRs are identified:
      (a) selecting one of the DRs; and
      (b) identifying the referenced record associated with the selected DR.

147. The apparatus of claim 146 wherein the processor selects by selecting the first DR.

148. The apparatus of claim 146 wherein a resolution rule set (RRS) exists for determining which of two overlapping DRs to select and the processor selects by applying the RRS to the overlapping DRs.

149. The apparatus of claim 146 wherein at least one long DR includes a short DR and additional text and wherein the processor selects by selecting the longest DR.

150. The apparatus of claim 146 wherein the processor analyzes by using natural language processing to identify DRs.

151. An apparatus for searching for a plurality of data references in a record which includes terms which form record phrases, each data reference characterized by a number of terms and a number of characters, the data references arranged in a table, each data reference in the table beginning with a first character construct, the data references organized such that their first character constructs are alphabetically ordered, each set of data references which begin with the same character construct forming a data reference sub-set, the apparatus comprising:
a processor running pulse sequencing program to perform the steps of:
  a) identifying a first term in the record as a current term;
  b) identifying a first character construct in the current term;
  c) identifying a data reference sub-set which begins with the current term first character construct;
  d) identifying a data reference from the sub-set as a current data reference;
  e) identifying the number of terms T in the current data reference;
  f) identifying the current term and the following (T-1) terms in the record as a current segment;
  g) determining if the current segment forms a single phrase;
    I) if the current segment forms a single phrase:
      1) identifying the number of characters in the current data reference;
      2) determining if the current segment includes the same number of characters as the current data reference;
        a) if the current segment includes the same number of characters as the current data reference:
          i) comparing the text of the current segment to the current data reference text to determine if the texts are identical:
            if the texts are identical, performing a function and then determining if there is at least one record term which follows the last current segment term and, if there is at least one record term which follows the last current segment term, selecting the term which follows the current segment as the current term and repeating steps (b) through (g);
            else, skip to step (g)(II)(1);
    II) else:
      1) determining if all of the sub-set data references have been compared to a segment beginning with the current term, and, if all of the sub-set data references have been compared to a segment beginning with the current term, skipping to step (h), else, selecting another sub-set data reference as the current data reference and repeating steps (e) through (g);

h) selecting the term following the current term as a new current term and repeating steps (b) through (g).

152. The apparatus of claim 151 wherein the first character construct is the first character of the first term.

153. The apparatus of claim 151 wherein the first character construct includes the characters of the first term.

154. A apparatus for searching for at least one data reference in a record which includes terms which form record phrases wherein the data reference is characterized by at least a first quantifiable data reference length characteristic, the apparatus comprising:

a processor running a pulse sequencing program to perform the steps of:
a) identifying a data reference as a current data reference;
b) identifying a first value which is the value of the current data reference first length characteristic;
c) identifying a record phrase to be searched; and
d) comparing the record phrase first length characteristic and the first value; and
   1) if the record phrase first length characteristic and first value are identical, comparing phrase text to current data reference text to determine if the phrase text and current data reference text are identical and, if identical, performing a function;
   2) else, concluding that the record phrase and the current data reference are different.

155. The apparatus of claim 154 wherein the data reference is a first data reference and there are a plurality of additional data references, each additional reference having a reference specific first length characteristic value and, wherein, the processor further performs the steps of:
(e) when it is concluded that the current data reference and the phrase are different, repeating steps (b) through (d) with another of the data references as the current data reference; and
(f) repeating step (e) for each of at least a sub-set of the additional data references.

156. The apparatus of claim 155 wherein the first length characteristic is a data reference term count.

157. The apparatus of claim 156 wherein the data references and term counts are correlated in a lookup table and wherein the processor identifies a current value by identifying the term count in the table.

158. The apparatus of claim 157 wherein each data reference in the table begins with a data reference specific first character construct, the data references are organized such that their constructs are alphabetically ordered, each set of data references which begin with the same character construct forms a data reference sub-set and the processor further performs the steps of, prior to identifying a data reference, identifying a term in a record which will form the first term in the record phrase, identifying the first character construct in the identified term, identifying the data reference sub-set which includes data references which begin with the first character construct in the term and limiting the search to the identified data reference sub-set.

159. The apparatus of claim 158 wherein the first character construct is the first character of the identified term.

160. The apparatus of claim 158 wherein the first character construct includes the characters in the identified term.

161. The apparatus of claim 158 wherein data references within a sub-set are searched in an order which is a function of the relative data reference term counts.

162. The apparatus of claim 161 wherein data references with relatively larger term counts are searched prior to data references with relatively shorter term counts.

163. The apparatus of claim 162 wherein each data reference is also characterized by a second length characteristic and the table also correlates each data reference with a second value which is a second length characteristic value and, wherein, the processor further performs the steps of, after determining that the record phrase first length characteristic and the first value are identical and prior to comparing the phrase and data reference texts, identifying the second value corresponding to the current data reference, comparing the record phrase second length characteristic and the second value, if the second record phrase characteristic and the second value are identical, comparing the text, else concluding that the record phrase and the current data reference are different.

164. The apparatus of claim 163 wherein the second value indicates the data reference character count.

165. The apparatus of claim 164 wherein the apparatus is for searching for all data references within a record and wherein the processor repeats the steps for at least a sub-set of all record phrases within a record.

166. The apparatus of claim 165 wherein record phrases are searched consecutively beginning with the first record phrase and ending with the last record phrase and, wherein, when a data reference and a specific record phrase are identical, the next phrase to be searched begins with the term immediately following the specific record phrase.

167. The apparatus of claim 166 wherein the record includes a plurality of terms, the step of identifying a record phrase including the steps of, after identifying the number of terms in a data reference, selecting a record segment as a segment beginning with a record term and including the number of terms in the data reference, the processor comparing the record phrase first length characteristic and the data reference first length characteristic value by determining the number of terms in a record phrase by determining if the terms in the record segment constitute a single phrase, where the terms in the record segment constitute a single phrase, determining that the record phrase first length characteristic is identical to the data reference first length characteristic, else concluding that the record phrase and the current data reference are different.

168. The apparatus of claim 154 wherein the first length characteristic is a data reference term count.

169. The apparatus of claim 168 wherein the data reference is also characterized by a second length characteristic and, wherein, the processor further performs the steps of identifying a second data reference length characteristic value which is a second value and, after determining that the record phrase first length characteristic and the first value are identical and prior to comparing the phrase and data reference texts, comparing the record phrase second length characteristic and the second value, if the second record phrase characteristic and the second value are identical, comparing the text, else concluding that the record phrase and the data reference are different.

170. The apparatus of claim 169 wherein the second length characteristic is a data reference character count.

171. The apparatus of claim 170 for use with a look-up table which correlates the data reference and the first and second values and wherein the processor identifies the data reference first and second values by identifying the values in the look-up table, respectively.

172. The apparatus of claim 154 wherein the first length characteristic is a data reference character count.

173. A apparatus for use with a system capable of recognizing specifying references (SRs) in a record which reference another record and forming links between the SRs and the referenced records, the apparatus for eliminating ambiguity when SRs overlap and comprising:

a processor running a pulse sequencing program to perform the steps of:
(i) receiving a referencing record;
(ii) analyzing the referencing record to identify SRs;
(iii) when two or more SRs overlap, enabling an operator to select at least one of the SRs;
(iv) identifying the referenced records associated with the selected SRs; and
(v) linking the selected SRs to corresponding records.

174. The apparatus of claim 173 wherein the processor enables by providing an SR list indicating possible SRs and providing a tool for selecting a sub-set of the SRs.

175. The apparatus of claim 174 wherein the processor links by presenting the selected SRs in a selectable format and linking the SRs to corresponding records such that when an SR is selected, the corresponding record is provided.

176. A apparatus for use with an application wherein specifying references (SRs) in one record to other records which are selectable to access the other records are visually distinguished from other record information so as to indicate selectability, the apparatus also for use with a system which enables a user to designate and also select SRs where designation comprises pointing to an SR without selection and, wherein a seemingly general SR is modified by other record information which renders the SR relatively specific, the apparatus for indicating the specific nature of an SR prior to selection and comprising:

a processor running a pulse sequencing program to perform the steps of:
when an SR is designated, indicating the specific nature of the SR.

177. The apparatus of claim 176 wherein the processor indicates by opening a description window and indicating the specific nature within the window.

178. The apparatus of claim 176 wherein SRs may overlap and, wherein, when SRs overlap and any portion of an overlapping SR is designated, the processor further performing the steps of indicating each of the overlapping SRs and enabling a user to select any one of the overlapping SRs for linking purposes.

179. A apparatus for use with an application wherein specifying references (SRs) in one record to other records which are selectable to access the other records are visually distinguished from other record information so as to indicate selectability, the apparatus also for use with a system which enables a user to designate and also select SRs where designation comprises pointing to an SR without selection and, wherein some SRs may overlap, the apparatus for eliminating ambiguity when SRs overlap and comprising:

a processor running a pulse sequencing program to perform the steps of:
when SRs overlap and any portion of an overlapping SR is designated, indicating each of the overlapping SRs and enabling a user to select any one of the overlapping SRs for linking purposes.

180. The apparatus of claim 179 wherein the processor indicates by opening a description window and indicating each of the overlapping SRs.

181. An apparatus for identifying a referenced record referenced in a referencing record wherein the referenced record is referenced in the referencing record by at least a data reference (DR), the apparatus comprising:

a processor running a pulse sequencing program to perform the steps of:
(i) receiving the referencing record;
(ii) analyzing the referencing record to identify a DR;
(iii) when a DR is identified, associating the DR and the referenced record;
wherein DRs include text and at least one long DR includes a short DR and additional text and wherein, when the long DR appears in the text, the processor analyzes to identify the DR by identifying the long DR.

182. An apparatus for identifying a referenced record referenced in a referencing record wherein the referenced record is referenced in the referencing record by at least a data reference (DR), the apparatus comprising:

a processor running a pulse sequencing program to perform the steps of:
(i) receiving the referencing record;
(ii) analyzing the referencing record to identify a DR;
(iii) when a DR is identified, associating the DR and the referenced record;
wherein a modifier reference (MR) can be used in conjunction with a DR to reference a record and at least one record is referenced by a DR/MR combination and the processor further performs the steps of:
after identifying the DR and prior to associating the DR, examining the record for an MR and, when an MR is identified, associating the DR/MR combination with the referenced record.

183. An apparatus for identifying a referenced record referenced in a referencing record wherein the referenced record is referenced in the referencing record by at least a data reference (DR), the apparatus comprising:

a processor running a pulse sequencing program to perform the steps of:
(i) receiving the referencing record;
(ii) analyzing the referencing record to identify a DR; and
(iii) when a DR is identified, associating the DR and the referenced record;
wherein the processor further performs the steps of, after the step of associating, monitoring changes to the record and when an associated DR is modified, changing the association.

184. The apparatus of claim 183 wherein the processor changes the association by eliminating the association.

185. A method for identifying a referenced record referenced in a referencing record wherein the referenced record is referenced in the referencing record by at least a data reference (DR), the method comprising the steps of:
(i) receiving the referencing record;
(ii) analyzing the referencing record to identify a DR;
(iii) when a DR is identified, associating the DR and the referenced record; and
(iv) wherein DRs include text and at least one long DR includes a short DR and additional text and wherein, when the long DR appears in the text, the step of analyzing to identify the DR includes identifying the long DR.

186. The method of claim 185 wherein the step of analyzing includes analyzing the record as the record is created.

187. The method of claim 186 wherein the step of identifying includes displaying the DR in an alternate format.

188. The method of claim 186 wherein the step of associating includes one of creating a hyperlink between the DR and the referenced record and accessing the referenced record.

189. The method of claim 185 further including monitoring changes to the referencing record and when text proximate or within the DR is modified, repeating steps (ii) through (iv).

190. A method for identifying a referenced record referenced in a referencing record wherein the referenced record is referenced in the referencing record by at least a data reference (DR), the method comprising the steps of:

(i) receiving the referencing record;

(ii) analyzing the referencing record to identify a DR;

(iii) when a DR is identified, associating the DR and the referenced record; and (iv) wherein a modifier reference (MR) can be used in conjunction with a DR to reference a record and at least one record is referenced by a DR/MR combination and the method further includes the steps of:

after identifying the DR and prior to associating the DR, examining the record for an MR and, when an MR is identified, associating the DR/MR combination with the referenced record.

191. The method of claim 190 wherein the DR and MR of a DR/MR combination are adjacent.

192. The method of claim 190 wherein the DR and MR of a DR/MR combination are separated by at least one other word.

193. A method for identifying a referenced record referenced in a referencing record wherein the referenced record is referenced in the referencing record by at least a data reference (DR), the method comprising the steps of:

(i) receiving the referencing record;

(ii) analyzing the referencing record to identify a DR;

(iii) when a DR is identified, associating the DR and the referenced record;

the method further including the steps of, after the step of associating, monitoring changes to the record and when an associated DR is modified, changing the association.

194. The method of claim 193 wherein the step of changing the association includes eliminating the association.

* * * * *

UNITED STATES PATENT AND TRADEMARK OFFICE
CERTIFICATE OF CORRECTION

PATENT NO. : 6,516,321 B1 Page 1 of 1
DATED : February 4, 2003
INVENTOR(S) : Carlos de la Huerga It is certified that error appears in the above-identified patent and that said Letters Patent is hereby corrected as shown below:

Title page,
Item [63], Related U.S. Application Data
"Continuation-in-part of application No. 09/326,177, filed on Jun. 4, 1999, which is a continuation-in-part of application No. 09/247,349, filed on Feb. 10, 1999, which is a continuation-in-part of application No. 09/130,934, filed Aug. 7, 1998, "which is a continuation-in-part of application No. 09/112,062, filed on Jul. 17, 1998" should be
-- Continuation-in-part of application No. 09/326,177 filed on June 4, 1999 which is a continuation-in-part of application No. 09/247,349 filed on February 10, 1999 which is a continuation-in-part of application No. 08/727,293 filed on October 9, 1996 which is a continuation-in-part of application No. 60/023,126 filed on July 30, 1996, the 09/247,349 application also claiming priority from application No. 08/871,818 filed on June 9, 1997. This application is also a continuation-in-part of application No. 09/130,934 filed on August 7, 1998. This application is also a continuation-in-part of application No. 09/112,062 filed on July 7, 1998. --

Column 26,
Line 22, "## - ######" should be -- ######## --.

Signed and Sealed this

First Day of July, 2003

JAMES E. ROGAN
*Director of the United States Patent and Trademark Office*